United States Patent
Barman et al.

(10) Patent No.: US 11,213,674 B2
(45) Date of Patent: *Jan. 4, 2022

(54) CATHETER ASSEMBLIES FOR NEUROMODULATION PROXIMATE A BIFURCATION OF A RENAL ARTERY AND ASSOCIATED SYSTEMS AND METHODS

(71) Applicant: Medtronic Ardian Luxembourg S.a.r.l., Luxembourg (LU)

(72) Inventors: Neil C. Barman, Mountain View, CA (US); Robert J. Beetel, Mountain View, CA (US); Benjamin J. Clark, Mountain View, CA (US); Andrew Wu, Mountain View, CA (US); Maria G. Aboytes, Mountain View, CA (US); Denise Zarins, Saratoga, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 182 days.

This patent is subject to a terminal disclaimer.

(21) Appl. No.: 16/291,689

(22) Filed: Mar. 4, 2019

(65) Prior Publication Data

US 2019/0269908 A1    Sep. 5, 2019

Related U.S. Application Data

(63) Continuation of application No. 13/458,877, filed on Apr. 27, 2012, now Pat. No. 10,258,791.

(51) Int. Cl.
*A61B 18/14* (2006.01)
*A61N 1/05* (2006.01)
*A61N 1/36* (2006.01)

(52) U.S. Cl.
CPC ........ *A61N 1/0558* (2013.01); *A61B 18/1492* (2013.01); *A61N 1/36007* (2013.01)

(58) Field of Classification Search
CPC .......... A61B 2018/00345; A61B 2018/00404; A61B 2018/00511; A61B 18/1492
See application file for complete search history.

(56) References Cited

U.S. PATENT DOCUMENTS

| 4,332,259 A | 6/1982 | McCorkle, Jr. |
| 4,602,624 A | 7/1986 | Naples et al. |
| (Continued) | | |

FOREIGN PATENT DOCUMENTS

| CN | 101489624 | 7/2009 |
| EP | 2029223 | 3/2009 |
| (Continued) | | |

OTHER PUBLICATIONS

Allen, E.V., Sympathectomy for essential hypertension, Circulation, 1952, 6:131-140.

(Continued)

*Primary Examiner* — Allen Porter
(74) *Attorney, Agent, or Firm* — Shumaker & Sieffert, P.A.

(57) ABSTRACT

Catheter assemblies for neuromodulation proximate a renal artery bifurcation and associated systems and methods are disclosed herein. A catheter assembly configured in accordance with a particular embodiment of the present technology can include a shaft having a proximal portion, a distal portion, and two therapeutic arms extending from the distal portion. The shaft can be configured to deliver the distal portion to a treatment site proximate a branch point or bifurcation in a renal blood vessel. The therapeutic arms can (Continued)

include energy delivery elements that are configured to deliver the therapeutically-effective energy to renal nerves proximate the branch point.

15 Claims, 16 Drawing Sheets

(56) References Cited

U.S. PATENT DOCUMENTS

| | | |
|---|---|---|
| 4,649,936 A | 3/1987 | Ungar et al. |
| 4,709,698 A | 12/1987 | Johnston et al. |
| 4,764,504 A | 8/1988 | Johnson et al. |
| 4,890,623 A | 1/1990 | Cook et al. |
| 4,928,688 A | 5/1990 | Mower |
| 4,976,711 A | 12/1990 | Parins et al. |
| 4,985,688 A | 1/1991 | Nagata |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,709,874 A | 1/1998 | Hanson et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster, Jr. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,212,434 B1 | 4/2001 | Scheiner |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,475,238 B1 | 11/2002 | Fedida |
| 6,488,679 B1 | 12/2002 | Swanson et al. |
| 6,506,189 B1 | 1/2003 | Rittman et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,790,222 B2 | 9/2004 | Kugler et al. |
| 6,827,726 B2 | 12/2004 | Parodi |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,884,260 B2 | 4/2005 | Kugler et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,942,692 B2 | 9/2005 | Landau et al. |
| 6,949,097 B2 | 9/2005 | Stewart et al. |
| 6,949,121 B1 | 9/2005 | Laguna |
| 7,108,715 B2 | 9/2006 | Lawrence-Brown et al. |
| 7,149,574 B2 | 12/2006 | Yun et al. |
| 7,162,303 B2 | 1/2007 | Levin et al. |
| 7,191,015 B2 | 3/2007 | Lamson et al. |
| 7,221,979 B2 | 5/2007 | Zhou et al. |
| 7,241,273 B2 | 7/2007 | Maguire et al. |
| 7,250,041 B2 | 7/2007 | Chiu et al. |
| 7,252,679 B2 | 8/2007 | Fischell et al. |
| 7,341,570 B2 | 3/2008 | Keren et al. |
| 7,343,195 B2 | 3/2008 | Strommer et al. |
| 7,364,566 B2 | 4/2008 | Elkins et al. |
| 7,381,200 B2 | 6/2008 | Katoh et al. |
| 7,390,894 B2 | 6/2008 | Weinshilboum et al. |
| 7,563,247 B2 | 7/2009 | Maguire et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 7,828,837 B2 | 11/2010 | Khoury |
| 7,853,333 B2 | 12/2010 | Demarais |
| 8,088,127 B2 | 1/2012 | Mayse et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,433,423 B2 | 4/2013 | Demarais |
| 8,805,545 B2 | 8/2014 | Zarins |
| 9,005,191 B2 | 4/2015 | Azamian et al. |
| 9,108,040 B2 | 8/2015 | Zarins |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill, III et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0105506 A1 | 6/2003 | Krishnan et al. |
| 2003/0125726 A1 | 7/2003 | Maguire et al. |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0167509 A1 | 8/2004 | Taimisto |
| 2004/0210270 A1 | 10/2004 | Erickson |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2005/0288730 A1 | 12/2005 | Deem et al. |
| 2006/0041277 A1 | 2/2006 | Deem et al. |
| 2006/0085054 A1 | 4/2006 | Zikorus et al. |

(56) References Cited

U.S. PATENT DOCUMENTS

| | | |
|---|---|---|
| 2006/0095029 A1 | 5/2006 | Young et al. |
| 2006/0206150 A1 | 9/2006 | Demarais et al. |
| 2006/0212076 A1 | 9/2006 | Demarais et al. |
| 2006/0235474 A1 | 10/2006 | Demarais |
| 2006/0247618 A1 | 11/2006 | Kaplan et al. |
| 2006/0247619 A1 | 11/2006 | Kaplan et al. |
| 2006/0271111 A1 | 11/2006 | Demarais et al. |
| 2007/0129720 A1 | 6/2007 | Demarais et al. |
| 2007/0162109 A1 | 7/2007 | Davila et al. |
| 2007/0208256 A1 | 9/2007 | Marilla |
| 2007/0265687 A1 | 11/2007 | Deem et al. |
| 2008/0319513 A1 | 12/2008 | Pu et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0264075 A1* | 10/2011 | Leung ................. A61B 18/02 604/528 |
| 2012/0130289 A1 | 5/2012 | Demarais et al. |
| 2012/0130345 A1 | 5/2012 | Levin et al. |
| 2012/0172837 A1 | 7/2012 | Demarais et al. |
| 2013/0072997 A1 | 3/2013 | Sanders et al. |
| 2013/0245726 A1 | 9/2013 | Zarins |
| 2013/0325000 A1 | 12/2013 | Bates |
| 2013/0331921 A1 | 12/2013 | Roubin |
| 2017/0021170 A1 | 1/2017 | Zarins |
| 2018/0021574 A1 | 1/2018 | Zarins |

FOREIGN PATENT DOCUMENTS

| | | |
|---|---|---|
| EP | 2320821 | 5/2011 |
| JP | 2009539565 | 11/2009 |
| WO | WO1994007446 | 4/1994 |
| WO | WO1995025472 | 9/1995 |
| WO | WO1995031142 | 11/1995 |
| WO | WO1997036548 | 10/1997 |
| WO | WO1998042403 | 10/1998 |
| WO | WO1999000060 | 1/1999 |
| WO | WO2001022897 | 4/2001 |
| WO | WO2001070114 | 9/2001 |
| WO | WO2003022167 | 3/2003 |
| WO | WO2003082080 | 10/2003 |
| WO | WO2005030072 | 4/2005 |
| WO | WO2005030072 | 5/2005 |
| WO | WO2005110528 | 11/2005 |
| WO | WO2006041881 | 4/2006 |
| WO | WO2006105121 | 10/2006 |
| WO | WO2007008954 | 1/2007 |
| WO | WO2007078997 | 7/2007 |
| WO | WO2007131015 | 11/2007 |
| WO | WO2007146834 | 12/2007 |
| WO | WO2008049084 | 4/2008 |
| WO | WO2009137819 | 11/2009 |
| WO | WO2013185138 | 12/2013 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. Vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study." Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renai Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis." Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16: 1 page.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter," Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

(56) References Cited

OTHER PUBLICATIONS

ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: Apr. 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltriais.gov/ct2/show/NCT01628198.
Opposition to European Patent No. 2465470, Granted Oct. 28. 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printput/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper, et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, Jun. 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-195545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1 756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages, <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page, <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension," St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny. "Conductive Keratoplasty For The Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine," Circulation, vol. 99, 1999, 7 pages.
Benito, F., et al. "Radiofrequency catheter ablation of accessory pathways in infants," Heart, 78:160-162 (1997).

(56) References Cited

OTHER PUBLICATIONS

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages,
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet The Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." Clin. Sci, 87: 13-19 (1994).
Hendee, W. R et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honor for renal denervation system." The (official blog of Medtronic Australasia, Nov. 12, 2012, 2 pages, <http://97waterlooroad.wordpress.com/2012/11/12/medtronic-awarded-industrys-highest-honour-for-renal-denervatlon-system/>.
Kaiser, Chris, AHA Lists Year's Big Advances in CV Research, medpage Today, Dec. 18, 2012, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531, 2:527-534 (2001).
Lee, S. J., et al. "Ultrasonic energy in endoscopic surqery." Yonsei Med J, 40:545-549 (1999).
Linz, Dominik et al., "Renal denervation suppresses ventricular arrhythmias during acute entricular ischemia in pigs," Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hvoertension." Circulation. 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010. 15 pages.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation In the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).

(56) References Cited

OTHER PUBLICATIONS

Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN 1 trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages
Miller, Reed, "Finding A Future For Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension, 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Henegar et al., "Catheter-Based Radiofrequency Renal Denervation: Location Effects on Renal Norepinephrine." American Journal of Hypertension, Ltd. 2015, 6 pages.
Search Report and Written Opinion dated Jul. 2, 2008 for PCT Application No. PCT/US0207/070799.
Search Report dated Aug. 4, 2011 for European Application No. 07793341.9.
Search Report dated Aug. 4, 2011 for European Application No. 07798341.9.
Search Report and Written Opinion dated Jul. 2, 2008 for PCT Application No. PCT/US2007/070799.
EP Appln No. 17163337.3-1659, Extended European Search Report, dated Jun. 30, 2017, 10pgs.
EP Application No. 07798341.9-1115, Office Communication dated Feb. 27, 2018, 6 pages.
European Search Report for European Application No. 13159256, dated Oct. 17, 2013, 6 pages.

* cited by examiner

*Arterial Vasculature*

*Venous Vasculature*

US 11,213,674 B2

CATHETER ASSEMBLIES FOR NEUROMODULATION PROXIMATE A BIFURCATION OF A RENAL ARTERY AND ASSOCIATED SYSTEMS AND METHODS

CROSS-REFERENCE TO RELATED APPLICATIONS

This application is a Continuation of U.S. patent application Ser. No. 13/458,877, filed Apr. 27, 2012, now U.S. Pat. No. 10,258,791, the disclosure of which is incorporated herein by reference in its entirety.

TECHNICAL FIELD

The present technology relates generally to neuromodulation therapies. In particular, several embodiments of the present technology are directed to catheter assemblies for neuromodulation proximate a bifurcation of a renal artery and associated methods and systems.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys of plasma is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery (e.g., via radiofrequency (RF) ablation) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

DETAILED DESCRIPTION

Figure 1:
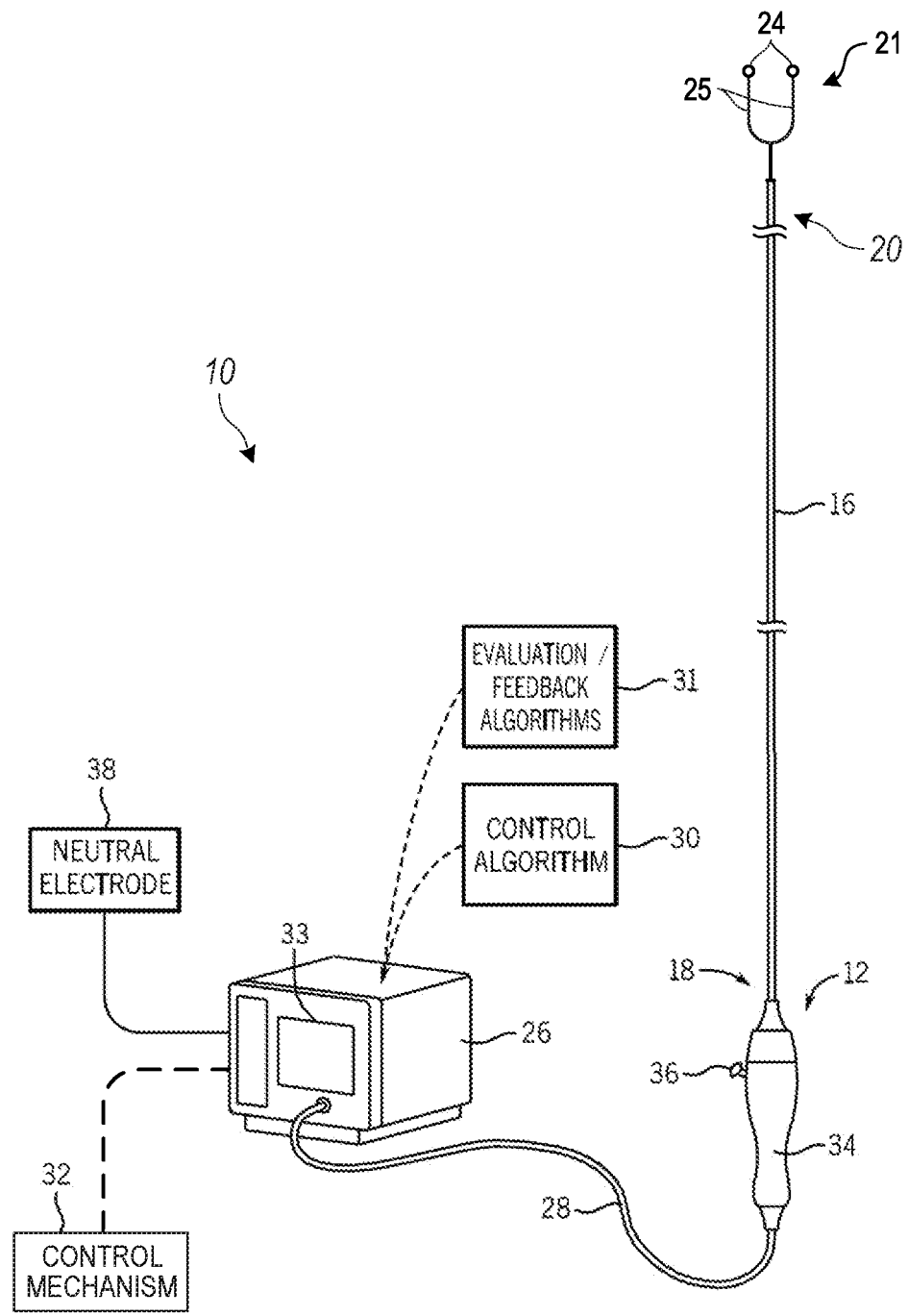
FIG. 1 is a partially schematic diagram of a neuromodulation system configured in accordance with an embodiment of the present technology.

The present technology is directed to apparatuses, systems, and methods for achieving electrically- and/or thermally-induced renal neuromodulation (i.e., rendering neural fibers that innervate the kidney inert or inactive or otherwise completely or partially reduced in function) by percutaneous transluminal intravascular access. In particular, at least some embodiments of the present technology relate to catheters and catheter assemblies having therapeutic arms that deliver therapeutically-effective energy to renal nerves proximate a renal artery bifurcation. In other embodiments, the present technology may be used to apply ablative energy proximate (i.e., at or near) a bifurcation or branch point in other blood vessels and/or other organs within the human body (e.g., the heart).

Specific details of several embodiments of the technology are described below with reference to FIGS. 1-18. Although many of the embodiments are described below with respect to devices, systems, and methods for intravascular modulation of renal nerves using multi-electrode therapeutic assemblies, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-18.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. It is believed that renal nerves reside in close proximity to renal arteries within the adventitia of the renal arteries or otherwise within approximately 1 cm of the renal artery medial wall. The renal nerves are distributed randomly around the circumference of the renal artery. However, evidence suggests that the renal nerves congregate distal to the aorta and proximate (e.g., at or near) bifurcations or branch points of the renal artery (i.e., points at which the renal artery splits into two or more lumens). This concentration of renal nerves provides a relatively confined site at which therapeutically effective energy can be applied.

The incapacitation provided by neuromodulation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics. Additionally, osteoporosis can be sympathetically activated and might benefit from the downregulation of sympathetic drive that accompanies renal neuromodulation. A more detailed description of pertinent patient anatomy and physiology is provided in Section VI below.

Various techniques can be used to partially or completely incapacitate neural pathways, such as those innervating the kidney. The purposeful application of energy (e.g., electrical energy, thermal energy) to tissue by energy delivery element(s) can induce one or more desired thermal heating effects on localized regions of the renal artery and adjacent regions of the renal plexus, which lay intimately within or adjacent to the adventitia of the renal artery. The purposeful application of the thermal heating effects can achieve neuromodulation along all or a portion of the renal plexus.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity (RSNA) is expected.

Hypothermic effects may also provide neuromodulation. Cryotherapy, for example, may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

Cryotherapy has certain characteristics that can be beneficial for intravascular renal neuromodulation. For example, cryotherapies generally operate at temperatures that cause cryotherapeutic applicators to adhere to moist tissue. This can be beneficial because it promotes stable, consistent, and continued contact during treatment. The typical conditions of treatment can make this an attractive feature because, for example, a patient can move during treatment, a catheter associated with an applicator can move, and/or respiration can cause the kidneys to rise and fall and thereby move the renal arteries. In addition, blood flow is pulsatile and causes the renal arteries to pulse. Adhesion associated with cryotherapeutic cooling also can be advantageous when treating short renal arteries in which stable intravascular positioning can be more difficult to achieve.

II. Selected Embodiments of Neuromodulation Systems

FIG. 1 illustrates a neuromodulation system 10 ("system 10") configured in accordance with an embodiment of the present technology. The system 10 includes an intravascular catheter 12 operably coupled to an energy generator or energy source 26 (e.g., an RF energy generator, a cryotherapy console, etc.). The catheter 12 can include an elongated shaft 16 having a proximal portion 18, a handle 34 at a proximal region of the proximal portion 18, and a distal portion 20. The catheter 12 can further include a treatment section or therapeutic assembly 21 (shown schematically) at the distal portion 20 (e.g., attached to the distal portion 20, defining a section of the distal portion 20, etc.). As explained in further detail below, in certain embodiments the therapeutic assembly 21 can include two elongated members or arms 25 that each include at least one energy delivery element 24 (e.g., an electrode). The therapeutic assembly 21 can be delivered proximate to a bifurcation or branch point of a renal blood vessel (e.g., a renal artery) such that the arms 25 can each be positioned in separate branches of the renal blood vessel. The energy delivery elements 24 can be configured to deliver energy (e.g., RF energy, cryotherapeutic cooling, etc.) to the walls of the branched blood vessel and provide therapeutically-effective electrically- and/or thermally-induced renal neuromodulation at either side of the bifurcation (e.g., proximate a concentration of renal nerves).

The catheter 12 can be electrically coupled to the energy source 26 via a cable 28, and the energy source 26 (e.g., a RF energy generator) can be configured to produce a selected modality and magnitude of energy for delivery to the treatment site (e.g., proximate a renal artery bifurcation) via the energy delivery elements 24. A supply wire (not shown) can extend along the elongated shaft 16 or through a lumen in the shaft 16 to the energy delivery elements 24 and transmit the treatment energy to the energy delivery elements 24. In some embodiments, each energy delivery element 24 includes its own supply wire. In other embodiments, however, two or more energy delivery elements 24 may be electrically coupled to the same supply wire. A control mechanism 32, such as foot pedal or handheld remote control device, may be connected to the energy source 26 to allow the clinician to initiate, terminate and, optionally, adjust various operational characteristics of the energy source 26, including, but not limited to, power delivery. The remote control device (not shown) can be positioned in a sterile field and operably coupled to the energy delivery elements 24, and can be configured to allow the clinician to selectively activate and deactivate the energy delivery elements 24. In other embodiments, the remote control device may be built into the handle assembly 34.

The energy source 26 can be configured to deliver the treatment energy via an automated control algorithm 30 and/or under the control of a clinician. For example, the energy source 26 can include computing devices (e.g., personal computers, server computers, tablets, etc.) having processing circuitry (e.g., a microprocessor) that is configured to execute stored instructions relating to the control algorithm 30. In addition, the processing circuitry may be configured to execute one or more evaluation/feedback algorithms 31, which can be communicated to the clinician. For example, the energy source 26 can include a monitor or display 33 and/or associated features that are configured to provide visual, audio, or other indications of power levels, sensor data, and/or other feedback. The energy source 26 can also be configured to communicate the feedback and other information to another device, such as a monitor in a catheterization laboratory.

Figure 2:
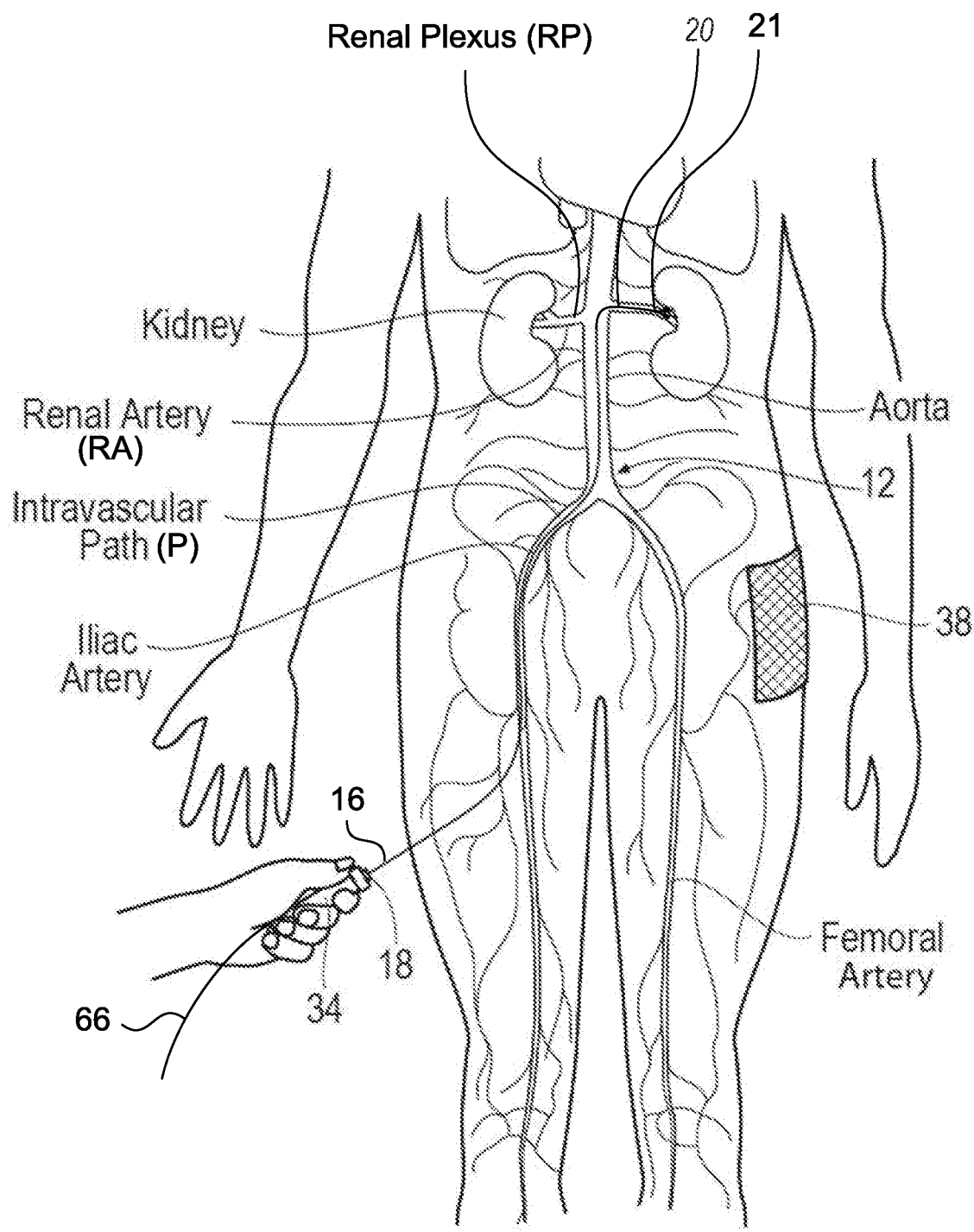
FIG. 2 illustrates modulating renal nerves with a catheter configured in accordance with an embodiment of the present technology.

In certain embodiments, the system 10 may be configured to deliver a monopolar electric field via the energy delivery elements 24. In such embodiments, a neutral or dispersive electrode 38 may be electrically connected to the energy generator 26 and attached to the exterior of the patient (e.g., as shown in FIG. 2). In other embodiments, the system 10 can deliver a bipolar electric field via the energy delivery elements 24 and/or other suitable forms of treatment energy, such as a combination of monopolar and bipolar electric fields. Additionally, the system 10 can include one or more sensors (not shown) located proximate to or within the energy delivery elements 24. For example, the system 10 can include temperature sensors (e.g., thermocouple, thermistor, etc.), impedance sensors, pressure sensors, optical sensors, flow sensors, and/or other suitable sensors connected to one or more supply wires (not shown) that transmit signals from the sensors and/or convey energy to the energy delivery elements 24.

FIG. 2 (with additional reference to FIG. 1) illustrates modulating renal nerves with an embodiment of the system 10. The catheter 12 provides access to a bifurcation or branch point of the renal artery RA through an intravascular path P, such as a percutaneous access site in the femoral (as shown in FIG. 2), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. In the embodiment illustrated in FIG. 2, the therapeutic assembly 21 is delivered intravascularly to the treatment site using a guide wire 66. The distal end of the therapeutic assembly 21 may define a passageway for engaging the guide wire 66 for delivery of the catheter 12 using over-the-wire ("OTW") or rapid exchange ("RX") techniques. At the treatment site, the guide wire 66 can be removed and the therapeutic assembly 21 can transform or otherwise be moved to a deployed arrangement for delivering energy at the treatment site. In other embodiments, the therapeutic assembly 21 may be delivered to the treatment site within a guide sheath (not shown). When the therapeutic assembly 21 is at the target site, the guide sheath may be at least partially withdrawn or retracted and the therapeutic assembly 21 can be transformed into the deployed arrangement. In other embodiments, the shaft 16 may be steerable itself such that the therapeutic assembly 21 may be delivered to the treatment site without the aid of the guide wire 66 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the therapeutic assembly 21. For example, a fluoroscopy system (e.g., including a flat-panel detector, x-ray, or c-arm) can be rotated to accurately visualize and identify the site of the renal artery bifurcation and its takeoff angle (i.e., the angle at which the branches extend distally from the renal artery RA with respect to one another), which may be obscured in the anterior-posterior (A-P) plane. In other embodiments, the site of the renal artery bifurcation can be determined using IVUS, OCT, and/or other suitable image mapping modalities that can correlate the site of the bifurcation with an identifiable anatomical structure (e.g., a spinal feature) and/or a radiopaque ruler (e.g., positioned under or on the patient) before delivering the catheter 12. Further, in some embodiments, image guidance components (e.g., IVUS, OCT) may be integrated with the catheter 12 and/or run in parallel with the catheter 12 to provide image guidance during positioning of the therapeutic assembly. For example, image guidance components (e.g., IVUS or OCT) can be coupled to at least one of the therapeutic assembly 21 (e.g., proximal to the therapeutic arms 25) to provide three-dimensional images of the vasculature proximate the bifurcation to facilitate positioning or deploying the therapeutic arms 25 within the correct branches of the RA or elsewhere proximate the bifurcation.

As discussed in greater detail below, after the therapeutic assembly 21 is delivered to the renal artery RA the arms 25 (FIG. 1) can be positioned in respective branches of the renal artery RA and the energy delivery elements 24 (FIG. 1) can be placed proximate to (e.g., in contact with) vessel walls of the branched renal artery (e.g., using a shaped stylus, guide wires, magnets, etc.). Energy is then purposefully applied via the energy delivery elements 24 to vessel walls to induce one or more desired neuromodulating effects on localized regions of the renal artery proximate the renal artery bifurcation and adjacent regions of the renal plexus RP, which lay intimately within, adjacent to, or in close proximity to the adventitia of the renal artery RA. The purposeful application of the energy may achieve neuromodulation along all or at least a portion of the renal plexus at both sites of the bifurcation.

The neuromodulating effects are generally a function of, at least in part, power, time, contact between the energy delivery elements 24 (FIG. 1) and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

III. Catheter Assemblies for Neuromodulation with Therapeutic Arms

Figure 3A:
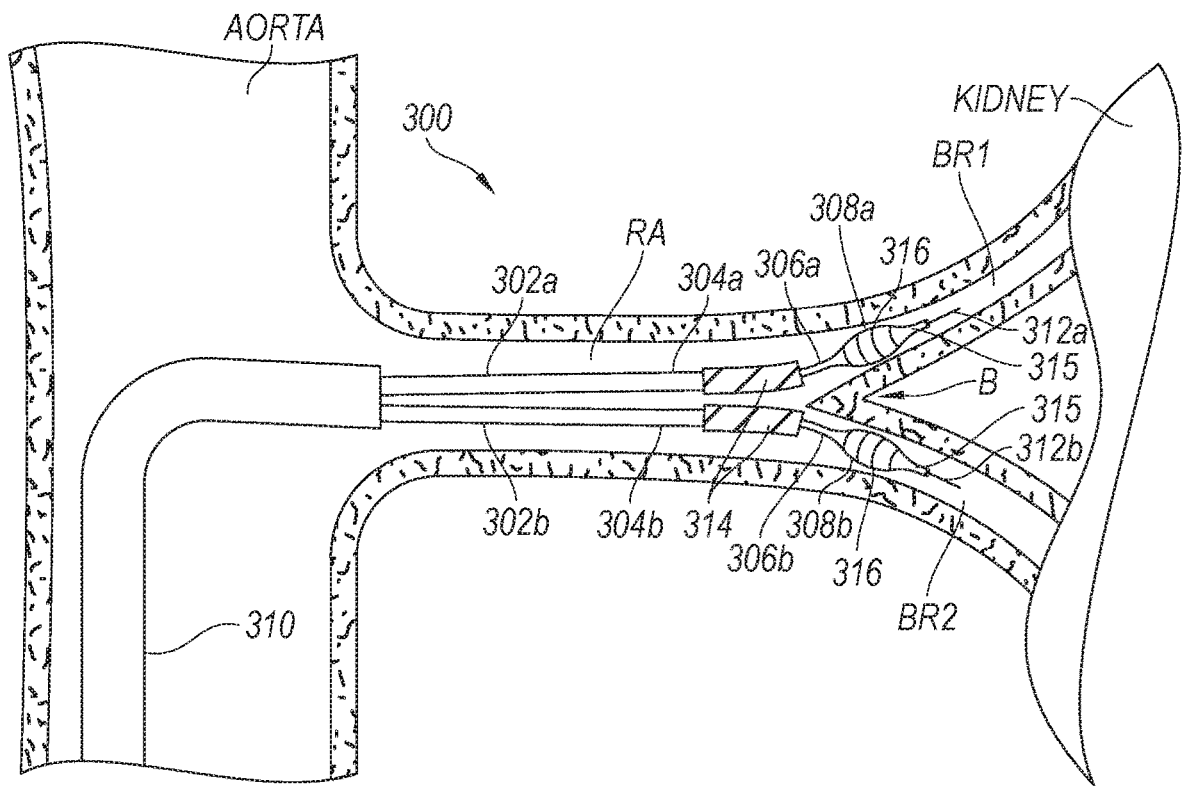
FIGS. 3A-3C are a partial cross-sectional views of a distal portion of a catheter assembly being delivered and deployed proximate a renal artery bifurcation in accordance with an embodiment of the present technology.
Figure 3B:
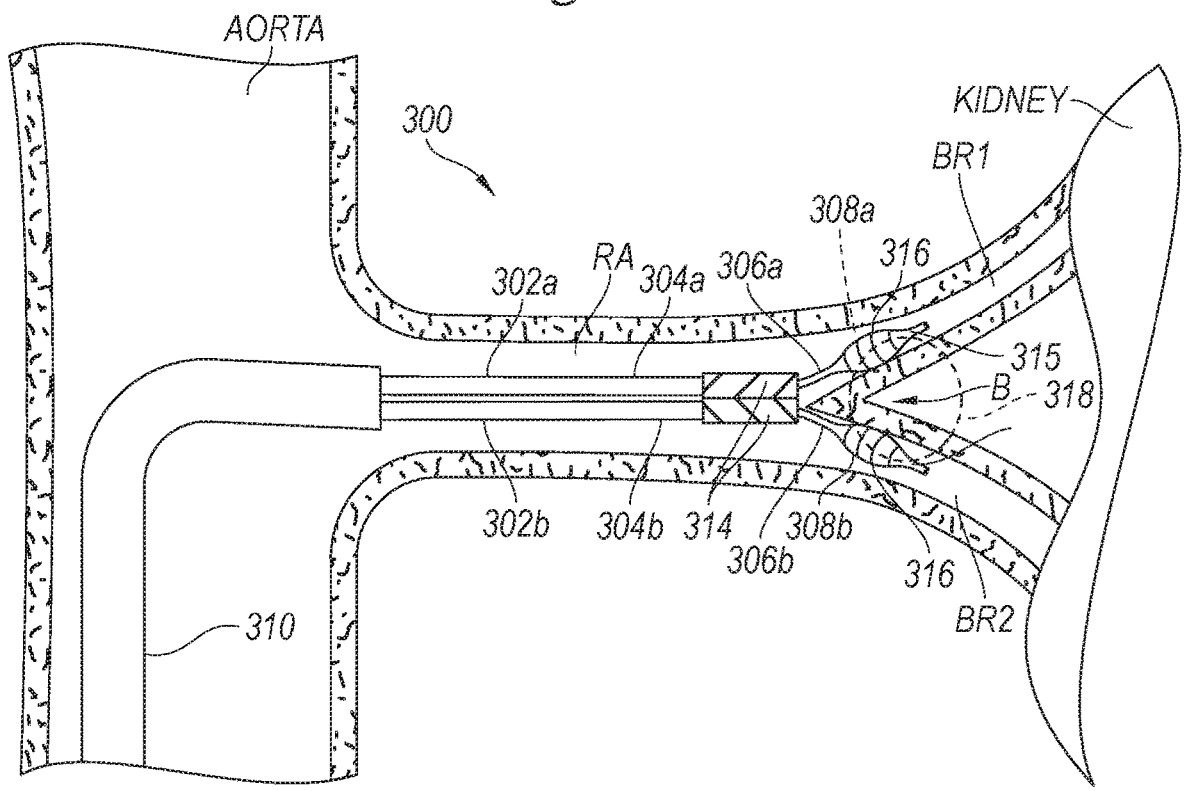
Figure 3C:
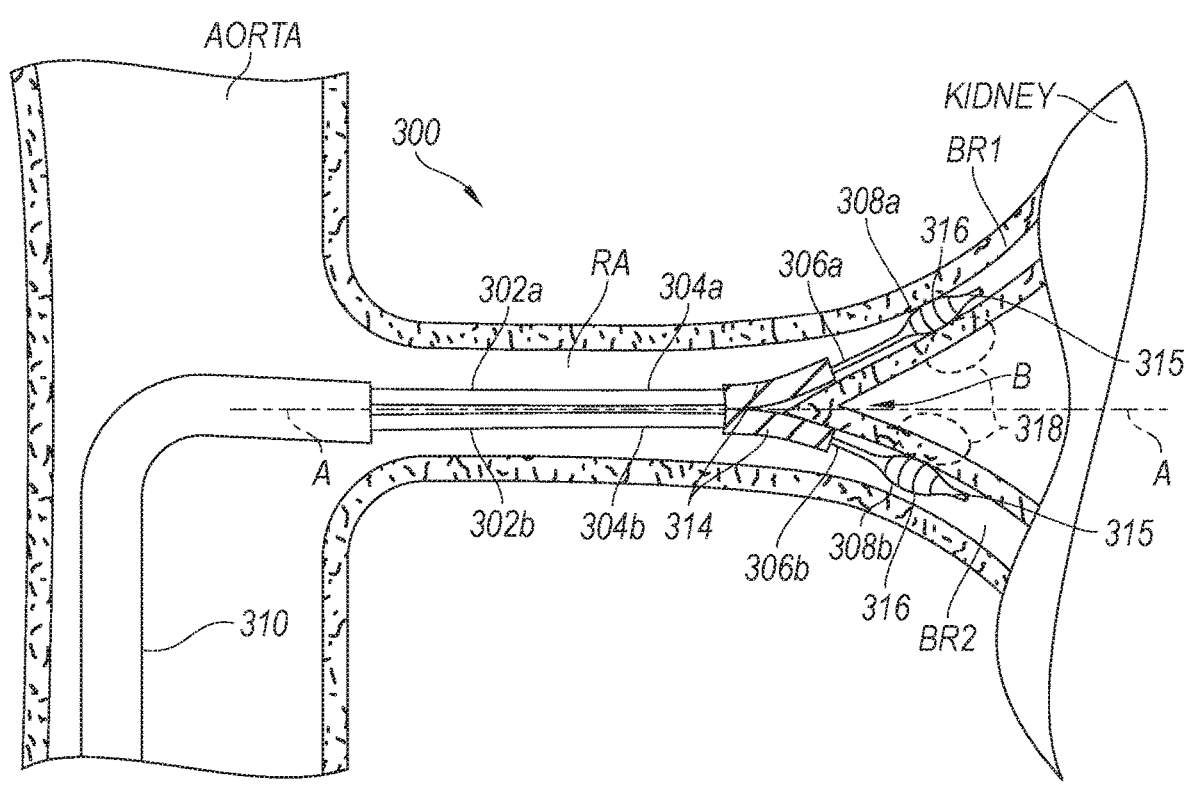

FIG. 3A is a partial cross-sectional view of a distal portion of a catheter assembly 300 being delivered to a treatment site proximate a bifurcation or branch point B of a renal artery RA in accordance with an embodiment of the present technology, and FIGS. 3B and 3C are partial cross-sectional views of the distal portion of the catheter assembly 300 of FIG. 3A deployed at the treatment site in accordance with embodiments of the present technology. As shown in FIGS. 3A-3C, the catheter assembly 300 can include a first catheter or elongated shaft 302a and a second catheter or shaft 302b (referred to collectively as "shafts 302") having distal portions 304a and 304b, respectively, and proximal portions (not shown). The distal portion 304a of the first shaft 302a can be defined at least in part by a first therapeutic member or arm 306a, and the distal portion 304b of the second shaft 302b can be defined at least in part by a second therapeutic member or arm 306b. The first and second therapeutic arms 306a and 306b can include first and second energy delivery elements 308a and 308b, respectively (referred to collectively as "energy delivery elements 308"), configured to deliver therapeutically-effective energy to a treatment site. The first and second arms 306a and 306b can be configured to be delivered proximate the bifurcation B of the renal artery RA at least partially into corresponding first and second branches BR1 and BR2 (collectively referred to as "branches BR") of the renal artery RA. The therapeutic arms 306a and 306b and the corresponding energy delivery elements 308a and 308b carried thereon can define a therapeutic assembly configured to modulate renal nerves proximate the bifurcation B of the renal artery RA.

The shafts 302 can be made from relatively flexible materials (e.g., polymers) to navigate the sometimes tortuous vasculature proximate the renal arteries, and the distal portions 304 may include braided and/or other semi-rigid structures that can support the therapeutic arms 306. The shafts 302 can be relatively small (e.g., microcatheters) such that they can be positioned together within the renal artery RA and, optionally, within a sheath or guide catheter 310 for delivery to the renal artery RA. In various embodiments, the proximal portions of the first and second shafts 302a and 302b can have a combined outer diameter or cross-sectional dimension that is less than the inner diameter or cross-sectional dimension of a guide catheter or sheath 310 to allow both shafts 302 to be delivered through the guide catheter 310. For example, the guide catheter 310 may have a French size of 8 or smaller (e.g., a 6 Fr guide catheter) to facilitate delivery into the renal artery RA, and the proximal portions of the outer diameters of the shafts 302 can be sized accordingly.

The distal portions 304 of the shafts 302 (e.g., the therapeutic arms 306), however, can be delivered sequentially into the branches BR, and therefore do not necessarily share the space within the guide catheter 310. Accordingly, the distal portions 304 of the shafts 302 may have larger outer cross-sectional dimensions or diameters than the outer dimensions of the proximal portions. In illustrated embodiment, for example, the first and second therapeutic arms 306a and 306b have bulbous distal sections that carry the corresponding energy delivery elements 308a and 308b. In other embodiments, however, the distal portions 304 of the shafts 302 can have other suitable enlarged configurations. In selected embodiments, for example, the shafts 302 can have substantially uniform cross-sectional dimensions along their lengths, and the energy delivery elements 308 can be made from a thicker material or structure (e.g., a larger diameter wire) to enlarge the cross-sectional dimensions of the distal portions 304 of the shafts 302. Such larger distal portions 304 can facilitate contact with adjacent vessel walls and may support larger energy delivery elements 308 (e.g., larger electrodes). In further embodiments, one or both of the shafts 302 can have substantially constant outer diameters along their proximal and distal portions. In still further embodiments, the guide catheter 310 can include separate lumens configured to receive the first and second shafts 302a or a separate guide catheter can be used for each shaft 302 such the shafts 302 do not share the same cross-sectional area and keep them spaced apart from one another. In selected embodiments, a lumen of the guide catheter 310 (e.g., a dedicated lumen or the same lumen as is used to deliver the shafts 302) may be used to deliver image guidance systems to the renal artery RA to facilitate positioning of the therapeutic arms 306.

The energy delivery elements 308 may include one or more electrodes positioned along the length of the therapeutic arms 306. In the embodiment illustrated in FIGS. 3A-3C, for example, the energy delivery elements 308 are coiled electrodes 316 positioned proximal to the distal ends of the therapeutic arms 306, and formed from electrically conductive wires wound around the respective shafts 302. The diameter of the wires can be selected based, at least in part, on the desired thickness of each electrode 316 (e.g., thicker wire increases the diameter of the electrode 316) and/or the degree of energy transfer to be provided by each electrode 316. In other embodiments, the energy delivery elements 308 can include other types of electrodes and/or the electrodes 316 can be positioned elsewhere along the therapeutic arms 306. For example, the energy delivery elements 308 can include cylindrical band electrodes extending around at least a portion of each shaft 302, electrode tips having a bullet-like, spherical, and/or other atraumatic shape at the distal ends of the shafts 302, and/or spherical structures positioned proximal of the distal tips of the shafts 302. In further embodiments, the energy delivery elements 308 can have other suitable structures and/or multiple energy delivery elements 308 can be included on each therapeutic arm 306.

The energy delivery elements 308 can be configured to deliver various types of energy to the target tissue. In certain embodiments, for example, the energy delivery elements 308 can be configured to deliver continuous or pulsed RF energy (e.g., at about 400-600 kHz) in a monopolar and/or bipolar electric field. When applied in a bipolar electric field, the RF energy can be delivered across the two therapeutic arms 306 (i.e., across the carina ridge of tissue between the diverging vessels) between the first and second energy delivery elements 308a and 308b. In other embodiments, the energy delivery elements 308 can deliver RF energy independently of one another (i.e., in a monopolar fashion using a passive electrode attached to the outside of the patient), and the energy can be applied simultaneously, selectively, and/or sequentially. In embodiments including multiple energy delivery elements 308 on the therapeutic arms 306, the energy may be delivered between any desired combination of the energy delivery elements 308, such as in a bipolar electric field across two electrodes on a single therapeutic arm 306, in a bipolar electric field across the therapeutic arms 306, or selectively activated monopolar electric fields. This allows the clinician to select which energy delivery elements 308 may be used for power delivery in order to form highly customized lesion(s) having a variety of shapes or patterns. The energy delivery elements 308 can also be configured to deliver microwave energy, various types of electric energy, direct current (DC), alternating current (AC), high or low voltage, pulsed or non-pulsed), sonic energy (e.g., ultrasound energy or high intensity ultrasound (HIFU) energy), electroporation, electromagnetic radiation energy (e.g., infrared energy, laser energy, etc.), and/or other suitable forms of energy. For example, the energy delivery elements 308 can include electrodes specifically designed for electroporation and configured to pulse a high voltage electric field across the bifurcation B that provides electroporation-induced neuromodulation at the target site and can leave neighboring cells substantially unaffected. In other embodiments the energy delivery elements 308 can include RF electrodes that apply electric pulses across the bifurcation B, and thereby provide a combination of thermal ablation and electroporation. In further embodiments, the energy delivery elements 308 may be configured to provide direct thermal energy to the vessel walls using hot or cooled fluids (e.g., cryogenic cooling elements), hot or cooled elements, and/or thermoelectric effects (e.g., the Peltier effect). For example, the energy delivery elements 308 can be cryogenic applicators (e.g., cryoprobes and/or cryoballoons) that deliver therapeutically-effective cooling to the treatment site for neuromodulation.

As shown in FIG. 3A, the catheter assembly 300 can be delivered to the treatment site (e.g., proximate the bifurcation B of the renal artery RA) using the guide catheter 310 and first and second guide wires 312a and 312b (collectively referred to as guide wires 312) corresponding to the first and second shafts 302a and 302b. The guide catheter 310 can be inserted through the vasculature to the renal RA, and the first guide wire 312a can be advanced through the guide catheter 310 into the first branch BR1 of the renal artery RA, and the first shaft 302a can be passed through the guide catheter 310 along the first guide wire 312a (e.g., via a guide wire lumen extending through the first shaft 302a) such that the first therapeutic arm 306a extends beyond the bifurcation B at least partially into the first branch BR1. Similarly, the second shaft 302b can be advanced through the guide catheter 310 over the second guide wire 312b (e.g., through a guide wire lumen) at least partially into the second branch BR2 of the renal artery RA. In other embodiments, the first shaft 302a and the second shaft 302b can include or be attached to steerable members (e.g., pull wires) that can be used to navigate the shafts 302 to the treatment site. In various embodiments, the distal ends of the shafts 302 can include tapered or atraumatic tips 315 that can gently contact and/or deflect off of vessel walls as the shafts 302 navigate through vasculature to the treatment site.

As best seen in FIG. 3B, once the energy delivery elements 308 are positioned at their respective target sites within the branches BR of the renal artery RA, the guide wires 312 (FIG. 3A) can be removed from at least the distal portions 304 of the shafts 302, and the energy delivery elements 308 can be positioned at the vessel walls of the branches BR extending distally from the bifurcation B. The distal portions 304 of the shafts 302 can include magnets 314 that are configured to interact (e.g., attract) one another, and thereby draw the energy delivery elements 308 towards one another to facilitate positioning the energy delivery elements 308 proximate to (e.g., in contact with) the vessel walls extending distally from the bifurcation B. In the embodiment illustrated in FIG. 3B, the magnets 314 are proximal to the energy delivery elements 308 along the outer diameters of the shafts 302. In other embodiments, the magnets 314 can extend along the inner diameters of the shafts 302, be embedded in the shafts 302, be positioned within or distal to the energy delivery elements 308, and/or be positioned elsewhere along the shafts 302 that facilitates drawing the energy delivery elements 308 toward one another into contact with the vessel walls. The positioning of the magnets 314 and the strength of the magnetic field therebetween can be configured to account for the distance between the magnets 314 when positioned at the treatment (e.g., the distance between the branches BR) and/or other anatomical features (e.g., blood flow). In various embodiments, the guide wires 312 (FIG. 3A) can restrict the interaction of the magnets 314 during delivery of the catheter assembly 300, and removing the guide wires 312 (FIG. 3A) can allow the magnets 314 to attract the shafts 302 toward one another. In further embodiments, the magnets 314 can be configured to repel one another such that the energy delivery elements 308 are positioned proximate to or contact the vessel walls of the branches BR spaced apart from the bifurcation B.

The energy delivery elements 308 can also be drawn together and held in contact with the inner surfaces of the vessel walls using other suitable structures and devices. For example, the guide catheter 310, a separate catheter, or a sleeve (e.g., positioned within the guide catheter 310) can be advanced over both the first and second shafts 302a and 302b toward the bifurcation B to press the energy delivery elements 308 toward one another. Pre-shaped stylets (not shown) can be advance through the shaft 302 (e.g., via a guide wire lumen) after the guide wires 312 (FIG. 3A) have been removed to deflect the energy delivery elements 308 toward each other. In other embodiments, magnetic wires (not shown; e.g., wires having a magnetic core) can be advanced through the shafts 302 after the guide wires 312 (FIG. 3A) have been removed, and the magnetic field of the complementary magnetic wires can draw the energy delivery elements 308 together. The magnetic wires can include magnetic sections that extend along relatively short portions of the wires (e.g., only along the length of the energy delivery elements 308 when aligned therewith), or the magnetic sections can extend along longer portions of the length (e.g., several centimeters proximal to the energy delivery elements 308) to draw proximal portions of the shafts 302 together. As described in greater detail below, in other embodiments the energy delivery elements 308 can be drawn together using various other techniques.

Once the energy delivery elements 308 are positioned proximate to the vessel walls at the treatment site, the energy delivery elements 308 can deliver therapeutically-effective energy to modulate nerves proximate the bifurcation B of the renal artery RA. Since the renal nerves may be concentrated at or proximate to the carina of the bifurcation B (e.g., as compared to proximal portions of the renal artery RA proximate the aorta), the catheter assembly 300 is expected to provide neuromodulation to a large portion of the renal nerves at a single, confined treatment site. In addition, the neuromodulation energy is delivered to renal nerves from both sides of the bifurcation B, and therefore may provide a greater concentration of therapeutically-effective energy to a larger percentage of the renal nerves. For example, as shown in FIG. 3B, each energy delivery element 308 can deliver energy to a neuromodulation or treatment zone 318 proximate a bifurcation. In the illustrated embodiment, the treatment zones 318 of the first and second energy delivery elements 308a and 308b overlap to form a continuous treatment zone 318 at the carina of the renal artery bifurcation B (e.g., which may include a dense concentration of renal nerves). In other embodiments, however, the treatment zones 318 can be discrete. For example, the energy delivery elements 308 may be substantially aligned with one another within the branches BR as shown in FIG. 3B, but the treatment zones 318 of the individual energy delivery elements 308 may be smaller than those shown in FIG. 3B such that they do not overlap. As shown in FIG. 3C, in further embodiments the energy delivery elements 308 and corresponding treatment zones 318 can be offset from one another along a longitudinal axis A-A of the renal artery RA. For example, the first energy delivery element 308a can be advanced further along the axis A-A into the first branch BR1 than the second energy delivery element 308b such that the first energy delivery element 308a is positioned distal to the second energy delivery element 308b relative to the bifurcation B. The corresponding treatment zones 318 are therefore also offset from one another along the axis A-A of the renal artery RA and deliver neuromodulation energy to discrete portions of the branches BR. The offset energy delivery elements 308 can alternatively be configured to deliver sufficient neuromodulation energy to form offset, but overlapping, treatment zones 318.

In certain embodiments, a single energy delivery element 308 can be configured to deliver sufficient energy for neuromodulation proximate the bifurcation B. For example, the first energy delivery element 308a can deliver RF energy in a monopolar energy field that modulates renal nerves across the entire treatment zone 318 shown in FIG. 3B. In this embodiment, the second shaft 302b does not necessarily include an active energy delivery element, but can include a mechanism (e.g., the magnet 314) to facilitate drawing the first energy delivery element 308a toward the vessel wall (e.g., to contact the vessel wall). In other embodiments, the second shaft 302b can be omitted, and a pre-shaped stylet, deflectable tip, and/or other suitable mechanism may be used to facilitate positioning or wall contact for the first energy delivery element 308a.

Figure 4:
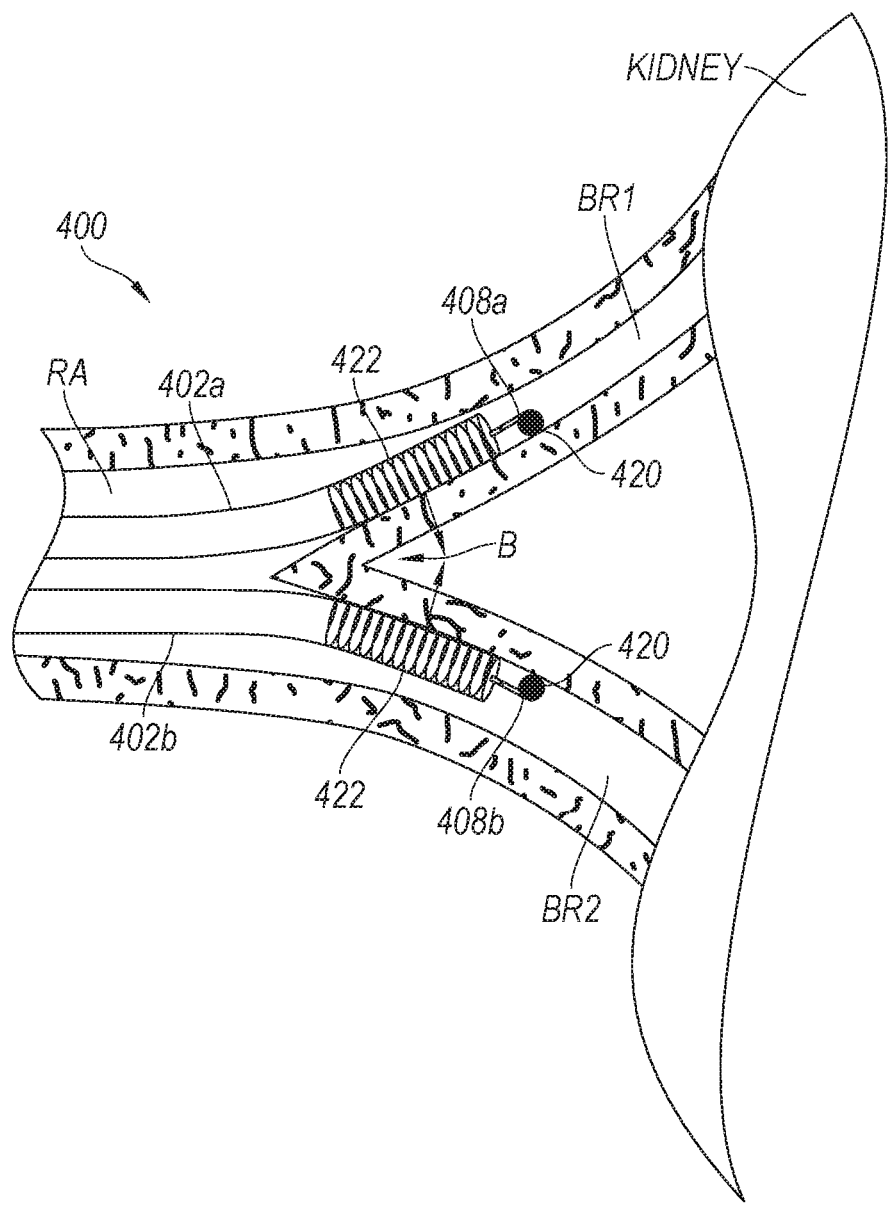
FIG. 4 is a partial cross-sectional view of a distal portion of a catheter assembly proximate a renal artery bifurcation in accordance with an embodiment of the present technology.

FIG. 4 is a partial cross-sectional view of a distal portion of a catheter assembly 400 deployed proximate a bifurcation B of a renal artery RA in accordance with another embodiment of the present technology. The catheter assembly 400 can include a number of features generally similar to the features of the catheter assembly 300 described above with reference to FIGS. 3A-3C. For example, the catheter assembly 400 can include first and second catheters or shafts 402a and 402b (referred to collectively as "shafts 402") that include corresponding first and second therapeutic arms 406a and 406b, respectively (referred to collectively as "therapeutic arms 406"), configured to extend into the branches BR of the renal artery RA proximate the bifurcation B. The therapeutic arms 406 can each include one or more energy delivery elements 408 (identified individually as a first energy delivery element 408a and a second energy delivery element 408b), such as spherical tip electrodes 420 at the distal ends of the therapeutic arms 406.

In the illustrated embodiment, the therapeutic arms 406 further include coil structures 422 positioned proximal to the tip electrodes 420 and configured to generate complementary electromagnetic fields (e.g., via a current delivered across the coil structures 422). The electromagnetic field can attract the tip electrodes 420 toward one another to facilitate contact with the vessel walls of the branches BR and enhance energy delivery. In other embodiments, one of the therapeutic arms 406 can include the coil structure 422 and the other therapeutic arm 406 may include a complimentary magnet or ferromagnetic material attracted to the coil structure 422 when an electromagnetic field is applied across it. In certain embodiments, the electromagnetic field generated by the coil structure(s) 422 can be strong enough to move the branches BR of the renal artery RA toward one another (e.g., as indicated by the arrows). In this embodiment, the energy can be concentrated to a more confined treatment zone that may include a higher density of renal nerves (e.g., because the nerves proximate the branches BR are constricted into a smaller area).

Figure 5A:
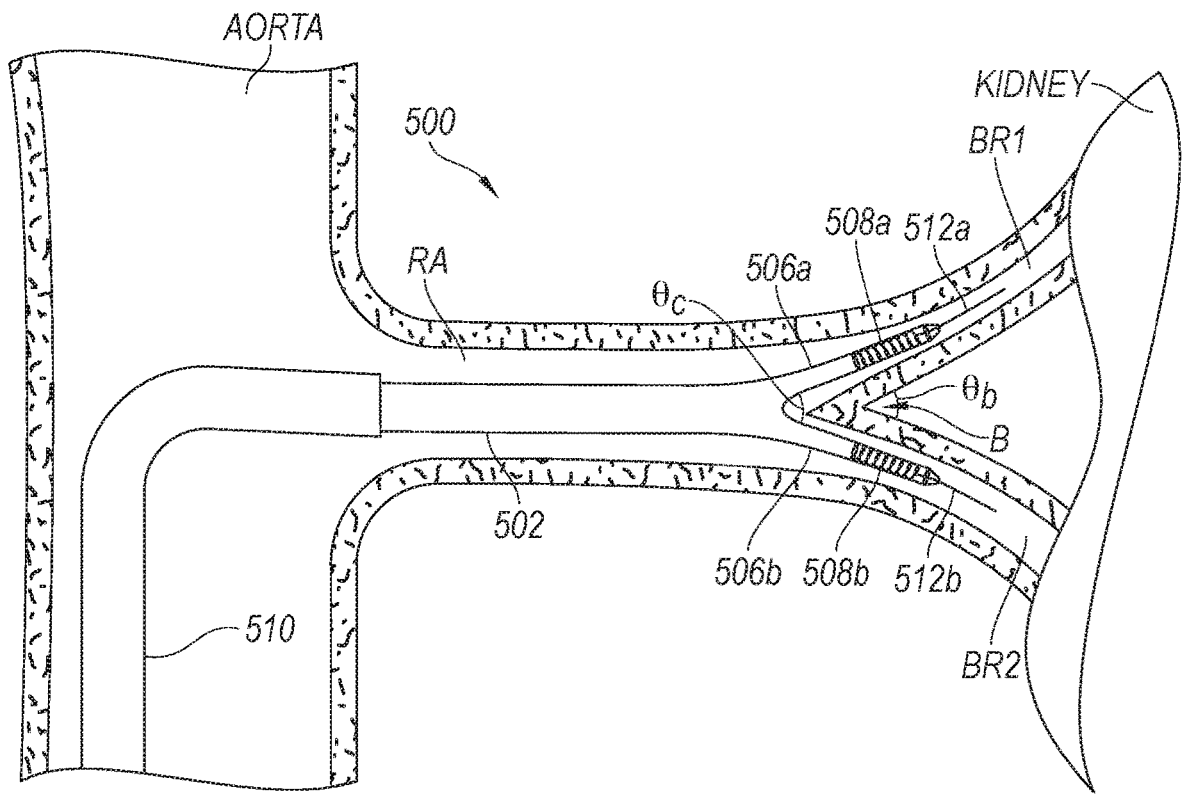
FIGS. 5A and 5B are a partial cross-sectional views of a distal portion of a catheter assembly being delivered and deployed proximate a renal artery bifurcation in accordance with another embodiment of the present technology.
Figure 5B:
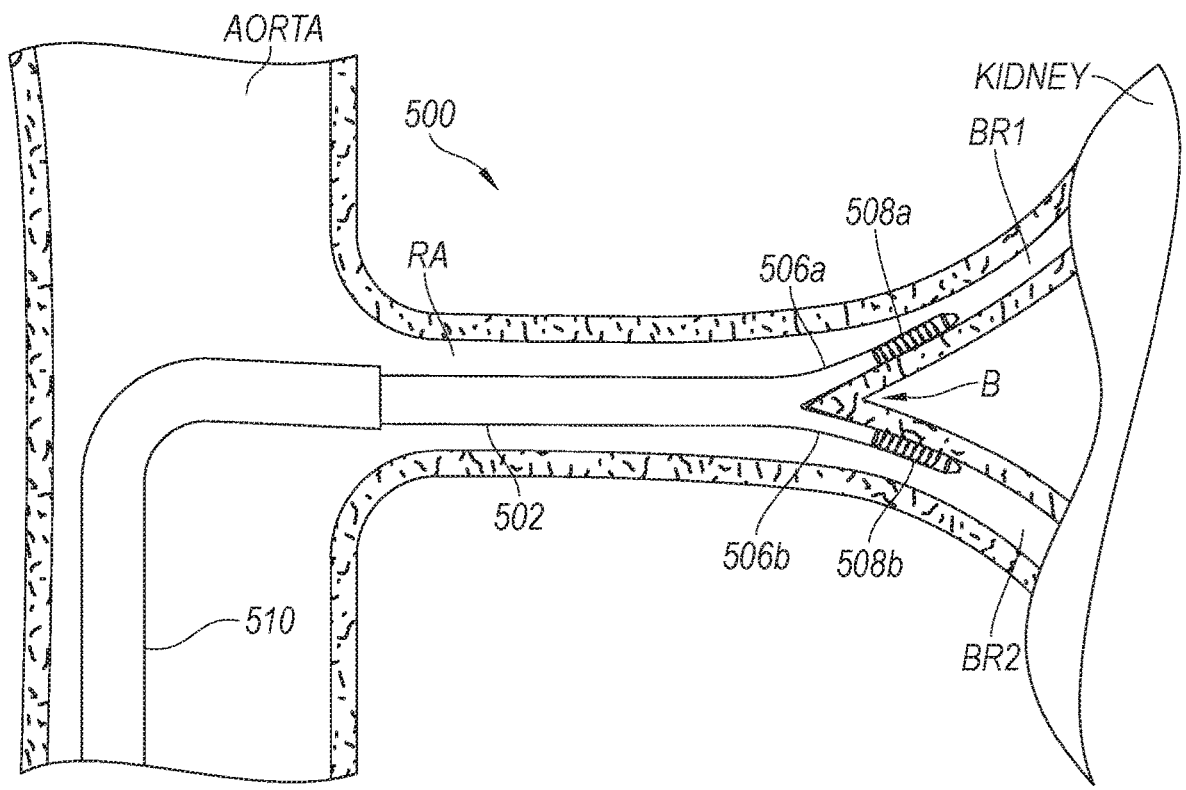

FIGS. 5A and 5B are partial cross-sectional views of a distal portion of a catheter 500 being delivered proximate a bifurcation B of a renal artery RA in accordance with another embodiment of the present technology. The catheter 500 can include several features generally similar to the features of the catheter assemblies 300 and 400 described above with reference to FIGS. 3A-4. For example, the catheter 500 can include first and second energy delivery elements 508a and 508b (referred to collectively as "energy delivery elements 508) carried by distal first and second therapeutic arms 506a and 506b, respectively (referred to collectively as "therapeutic arms 506"), that extend beyond the renal arty bifurcation B into respective branches BR. However, in the embodiment illustrated in FIGS. 5A and 5B, the therapeutic arms 506 are joined together at their proximal ends to a single shaft 502 (e.g., rather extending from two separate catheters). As shown in FIGS. 5A and 5B, the catheter assembly 500 with the bifurcated shaft 502 may have a deployed or open arrangement in which the therapeutic arms 506 extend distally from one another at an angle $\theta_c$ that at least generally corresponds to an angle $\theta_b$ of the bifurcation B of the renal artery RA to facilitate entry into the branches BR. In other embodiments, the angle $\theta_c$ between the therapeutic arms 506 can be less than the takeoff angle $\theta_b$ of the bifurcation B such that the distal end portions of the therapeutic arms 506 can be positioned in the ostium of the individual branches BR and pushed apart from one another as the therapeutic arms 506 are advanced distally into the corresponding branches BR. This configuration can force the therapeutic arms 506 and the energy delivery elements 508 positioned thereon against the adjacent tissue of the vessel wall to facilitate wall contact for energy delivery. In further embodiments, the angle θ between the therapeutic arms 506 can be larger than the takeoff angle $\theta_b$.

Referring to FIG. 5A, during delivery of the catheter assembly 500, a guide catheter or sheath 510 can be advanced into the renal artery RA (e.g., at or near the ostium of the renal artery RA) and first and second guide wires 512a and 512b (referred to collectively as "guide wires 512") can be advanced into each branch BR of the renal artery RA. The proximal ends (not shown) of the first and second guide wires 512a and 512b can then be positioned in the corresponding first and second therapeutic arms 506a and 506b, and the shaft 502 can be advanced over the guide wires 512 to the renal artery RA. At the renal artery RA, the therapeutic arms 506 can advance beyond the distal opening of the guide catheter 510, and the first and second guide wires 512a and 512b can direct the therapeutic arms 506 beyond the carina of the bifurcation B into the corresponding first and section branches BR1 and BR2 of the renal artery RA. In certain embodiments, the therapeutic arms 506 may be configured to deflect to the open configuration (e.g., with the angle $\theta_c$ between the therapeutic arms 506) when they are removed from the guide catheter 510 to track over the guide wires 512 positioned in the branches BR.

Referring to FIG. 5B, the energy delivery elements 508 can be drawn toward each other after the guide wires 512 are removed. In certain embodiments, pre-shaped stylets or wires with magnetic distal cores can be advanced through the shaft 502 after guide wire removal to facilitate positioning the energy delivery elements 508 at least proximate to the vessel walls of the branches BR. In other embodiments, the therapeutic arms 506 can have a pre-shaped bias that directs the energy delivery elements 508 into proximity or contact with the vessel walls. In this embodiment, the guide wires 512 (FIG. 5A) can direct or force the first therapeutic arm 506a and/or the second therapeutic arm 506b into a shape that facilitates entry into the corresponding branches BR (e.g., a generally straight shape). Once the therapeutic arms 506 are positioned at the target site (e.g., within the branches BR), the guide wires 512 may be removed from the therapeutic arms 506 to allow the therapeutic arms 506 to revert to their pre-shaped bias and contact the vessel walls. In further embodiments, the energy delivery elements 508 can be drawn toward one another using magnets positioned along the shaft 502, electromagnetic fields, and/or other suitable mechanisms that facilitate wall contact. Once wall contact has been made, the energy delivery elements 508 can apply therapeutically-effective energy to discrete or overlapping treatment zones to both sides of the concentration of renal nerves proximate the bifurcation B.

Figure 6:
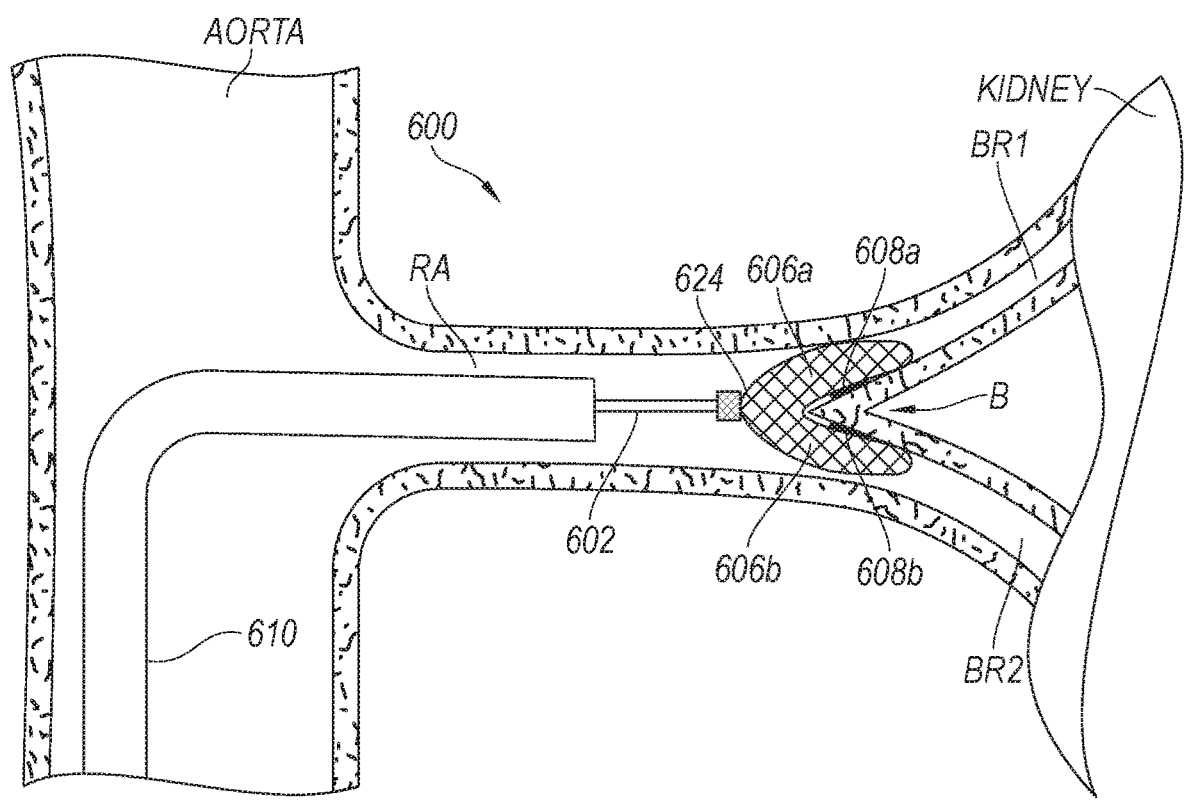
FIG. 6 is a partial cross-sectional view of a distal portion of a catheter assembly proximate a renal artery bifurcation in accordance with another embodiment of the present technology.

FIG. 6 is a partial cross-sectional view of a distal portion of a catheter assembly 600 proximate a bifurcation B of a renal artery RA in accordance with yet another embodiment of the present technology. The catheter assembly 600 can include a number of features generally similar to the features of the catheter assembly 500 described above with reference to FIGS. 5A and 58. However, in the embodiment illustrated in FIG. 6, the catheter assembly 600 includes a woven or mesh structure 624 that extends distally from a shaft 602. The mesh structure 624 can include a first therapeutic arm 606a and a second therapeutic arm 606b (referred to collectively as "therapeutic arms 606"), which carry corresponding first and second energy delivery elements 608a and 608b, respectively (referred to collectively as "energy delivery elements 608"). The therapeutic arms 606 can be defined by distally projecting portions of the mesh structure 624 or the body of the mesh structure 624.

In certain embodiments, the mesh structure 624 may be movable or transformable between a delivery or low-profile state (e.g., a radially collapsed mesh structure) that allows the mesh structure 624 to be delivered into the renal artery RA, and a deployed or expanded state (e.g., radially expanded) as shown in FIG. 6 after delivery to the renal artery RA. In the deployed state, the therapeutic arms 606 can extend at least partially into the branches BR and can be shaped such that the energy delivery elements 608 contact a portion of the vessel wall proximate the bifurcation B. The mesh structure 624 can be selectively transformable between the delivery and deployed states by manipulating a pull wire (not shown) that extends through the shaft 602, via automatic deployment using an actuator (e.g., on a remote control or on a proximal handle (not shown) of the catheter assembly 600), and/or other suitable deployment techniques. For example, the mesh structure 624 can include one or more braided wires that are not joined at the intersections and a pull wire attached at a distal portion of the mesh structure 624. The pull wire can be extended distally to contract or otherwise collapse the mesh structure 624 during delivery and can be pulled proximally at the treatment site to expand the mesh structure 624 to the configuration shown in FIG. 6. In certain embodiments, the mesh structure 624 can be collapsed or retracted (e.g., via a pull wire) after it has been positioned proximate the bifurcation B to draw the energy delivery elements 608 toward one another to enhance wall contact. In other embodiments, the mesh structure 624 can be made from a relatively flexible or soft material and have a cylindrical shape such that it can be delivered in an elongated or collapsed cylindrical shape and then expanded radially outwardly at the target site and pressed against the bifurcation B to wrap around the bifurcation B and extend into the branches BR.

Figure 7:
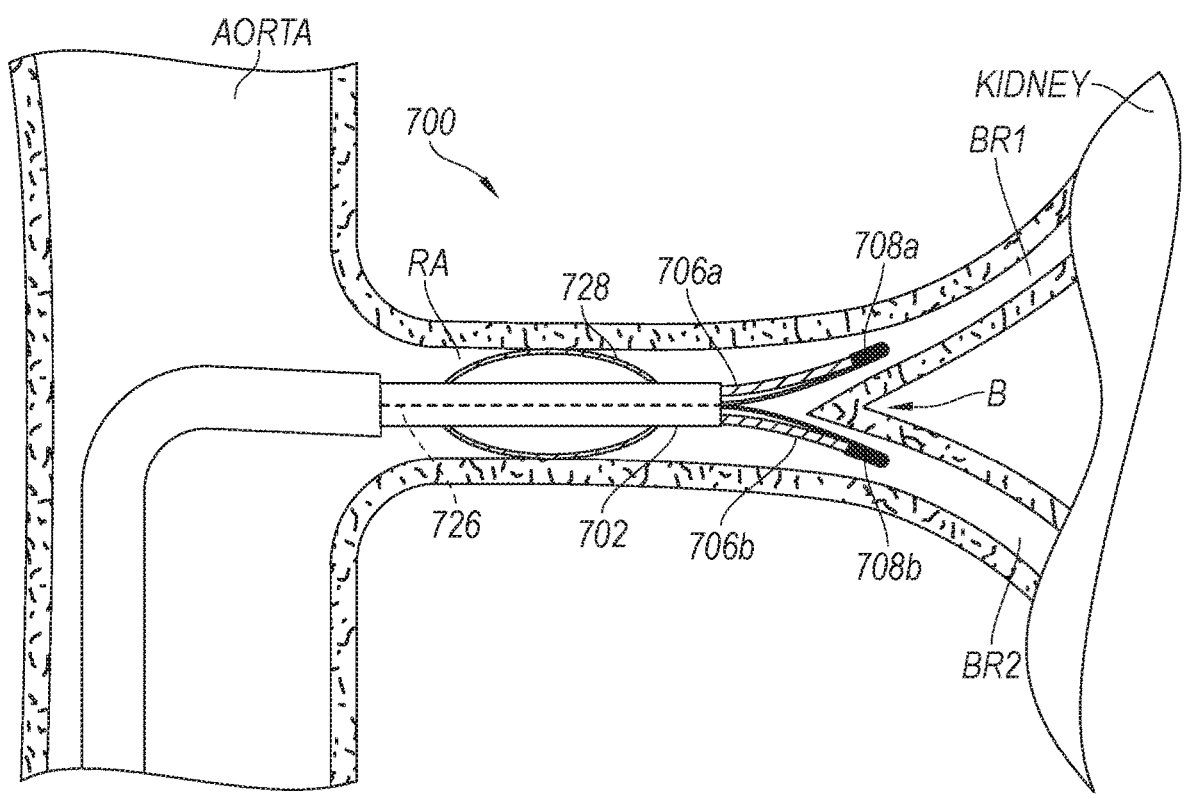
FIG. 7 is a partial cross-sectional view of a distal portion of a catheter assembly proximate a renal artery bifurcation in accordance with a further embodiment of the present technology.

FIG. 7 is a partial cross-sectional view of a distal portion of a catheter assembly 700 configured in accordance with a further embodiment of the present technology. The catheter assembly 700 includes several features generally similar to the features of the catheter assemblies 500 and 600 described above with reference to FIGS. 5A-6, such as first and second energy delivery elements 708a and 708b carried by first and second therapeutic arms 706a and 706b, respectively, that extend distally from a single shaft 702. In the embodiment illustrated in FIG. 7, the catheter assembly 700 further includes a pull line 726 (partially shown in broken lines) connected to distal end sections of the therapeutic arms 706 (e.g., at or near the energy delivery elements 708) and extending through the shaft 702 to a proximal end portion where it can be manipulated by a clinician. The pull line 726 can be made from a flexible wire material, a polymer material (e.g., as used for sutures), and/or other suitable materials. A clinician can manipulate the proximal end portion of the pull line 726 (e.g., by pulling it proximally) to pull or bend the energy delivery elements 708 toward one another and into stable contact against the vessel walls of the branches BR. In certain embodiments, the therapeutic arms 706 may be biased toward one another by a braided structure, laser-cut hypotubes (e.g., polymer or metal hypotubes), shape memory material (e.g., nitinol), and/or other suitable biased structures integrated with the therapeutic arms 706. In such embodiments, the biased therapeutic arms 706 can be urged toward one another by the pull line 726 by pulling it proximally.

As further shown in FIG. 7, the catheter assembly 700 may also include an expandable member 728 (e.g., an inflatable balloon) at the shaft 702 proximal to the bifurcation B of the shaft 702. The expandable member 728 can be delivered to the renal artery RA in a collapsed or low-profile delivery state and expanded to at least partially occlude the renal artery RA. For example, the expandable member 728 can be inflated with a gas (e.g., air or expanded refrigerant) and/or a liquid (e.g., saline solution, cooled fluid, etc.). The occlusion provided by the expandable member 728 can reduce or eliminate blood flow through the branches BR of the renal artery RA during energy delivery, and is expected to reduce the sometimes variable operational characteristics caused by blood flow. The expandable member 728 can also anchor the distal portion of the catheter assembly 700 in the renal artery RA to facilitate positioning the therapeutic arms 706 by stabilizing the shaft 702 in the renal artery RA and/or centering the shaft 702 in the renal artery RA. The expandable member 728 is an optional component that may not be included in some embodiments.

Figure 8A:
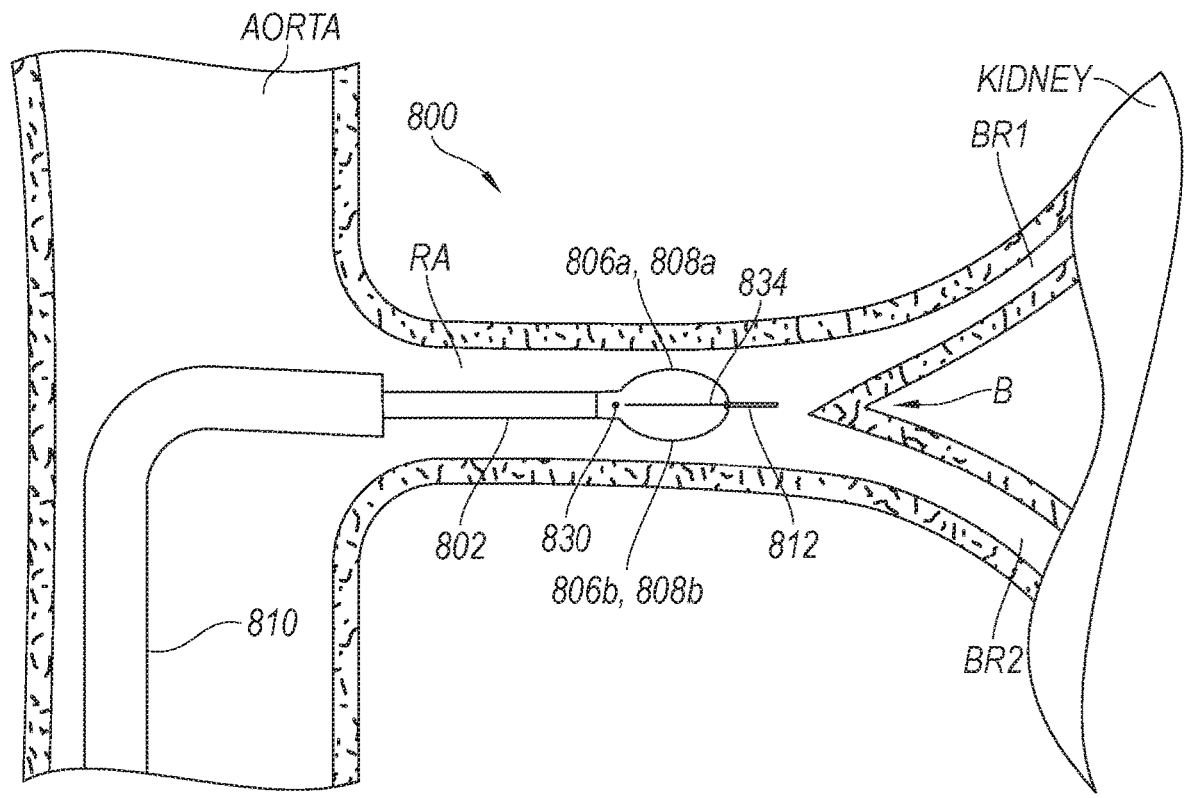
FIGS. 8A and 8B are a partial cross-sectional views of a distal portion of a catheter assembly being delivered and deployed proximate a renal artery bifurcation in accordance with a further embodiment of the present technology.
Figure 8B:
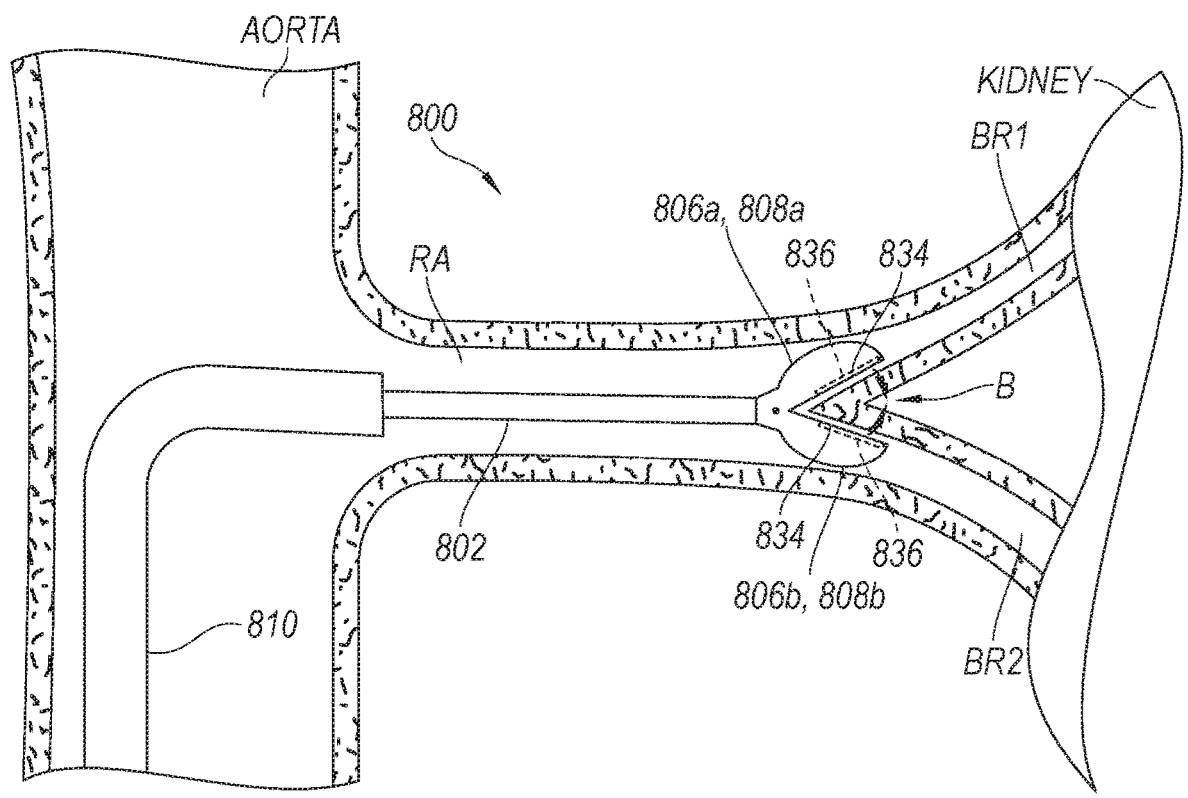

FIGS. 8A and 8B are a partial cross-sectional views of a distal portion of a catheter assembly 800 being delivered and deployed proximate a renal artery bifurcation B in accordance with an additional embodiment of the present technology. The catheter assembly 800 can include a number of features generally similar to the features of the catheter assemblies 500, 600, and 700 described above with reference to FIGS. 5A-7. In the illustrated embodiment, however, first and second therapeutic arms 806a and 806b (collectively referred to as "therapeutic arms 806") are coupled together at a joint 830 (e.g., a hinged joint) at a distal end portion of a shaft 802. The joint 830 is configured to allow the therapeutic arms 806 to pivot, rotate, or otherwise move from a closed or delivery state (FIG. 8A) to an open or deployed state (FIG. 8B) via remote activation, physical manipulation of one or more pull lines (e.g., attached to the distal ends of the therapeutic arms 806 and moved proximally or distally to move the therapeutic arms 806 toward or away from the bifurcation B), and/or other suitable actuators known to those skilled in the art for closing and opening joints. In the closed arrangement shown in FIG. 8A, inner surfaces 834 of the therapeutic arms 806 can abut one another such that the distal end portion of the catheter assembly 800 has a substantially low profile that facilitates intravascular delivery. In the open arrangement shown in FIG. 8B, the therapeutic arms 806 can splay at an angle to form a gap or space 834 sized and shaped to receive the carina of the bifurcation B such that the therapeutic arms 806 extend at least partially into the branches BR. Once positioned around the bifurcation B, the therapeutic arms 806 can be closed (e.g., as indicated by the arrows shown in FIG. 8B) to contact at least a portion of the inner surfaces 834 with the adjacent vessel walls.

In certain embodiments, the first and second therapeutic arms 806a and 806b can be made from a conductive material (e.g., a platinum iridium alloy) such that the entire jaw-like structure is electrically activated and serves as energy delivery elements 808. In other embodiments, portions of the therapeutic arms 806 include an insulated covering (e.g., via a polymer covering), or the therapeutic arms 806 may be composites of an insulative material and a conductive material. In these embodiments, discrete portions 836 (shown in broken lines in FIG. 8B) of each therapeutic arm 806 facing the inner walls can be electrically activated to serve as the energy delivery elements 808 and apply therapeutically-effective energy proximate the bifurcation B.

Figure 9:
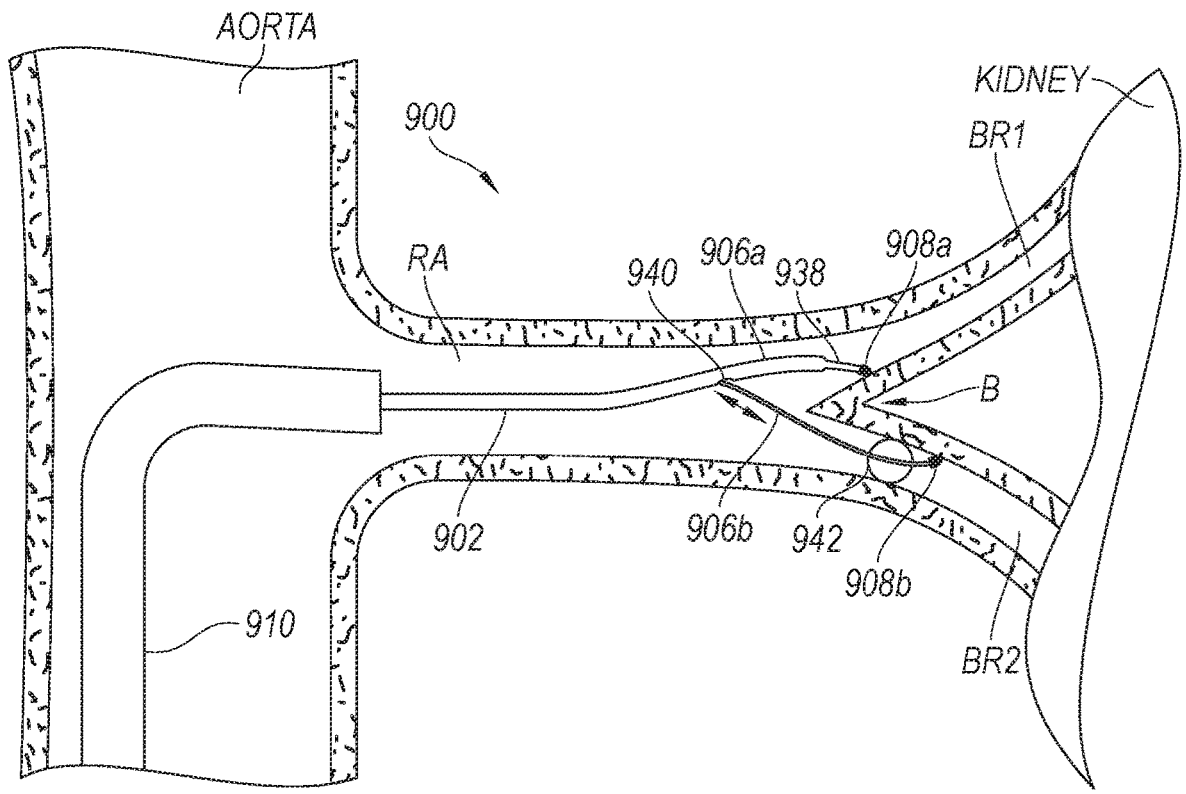
FIG. 9 is a partial cross-sectional view of a distal portion of a catheter assembly proximate a renal artery bifurcation in accordance with yet another embodiment of the present technology.

FIG. 9 is a partial cross-sectional view of a distal portion of a catheter assembly 900 proximate a renal artery bifurcation B in accordance with an additional embodiment of the present technology. The catheter assembly 900 can include a number of features generally similar to the features of the catheter assemblies described above. As shown in FIG. 9, however, rather than a bifurcated shaft, the catheter assembly 900 includes a shaft 902 that extends into a single first therapeutic arm 906a, which may be positioned within the first branch BR1 via a guide wire (not shown) as described above. The first therapeutic arm 906a can include a deflectable tip 938 and carries a first energy delivery element 908a (e.g., an electrode). The shaft 902 can further include an aperture or port 940 proximal to the first therapeutic arm 908a through which a second arm 906b carrying a second energy delivery element 908b can extend. The second arm 906b can be made from a pre-shaped member (e.g., a wire) that is bent or otherwise formed at its distal section to facilitate positioning the second electrode 908b at least proximate the arterial wall extending distally from the bifurcation B. For example, the second arm 906b can be made from a shape memory material (e.g., nitinol), an electroactive polymer (e.g., a piezoelectric material), and/or other suitable shapeable materials. In various embodiments, the second therapeutic arm 906b can be at least partially retracted into the shaft 902 via the aperture 940 (e.g., as indicated by the arrows shown in FIG. 9) during intravascular delivery. The second therapeutic arm 906b may include an atraumatic tip (e.g., the tapered atraumatic tip 315 shown in FIGS. 3A-3C) to gently contact the vessel walls as it is inserted into and retracted from the second branch BR2. At the renal artery RA, the second therapeutic arm 906b may be advanced distally through the aperture 940 until it is positioned within the second branch BR2 proximate the bifurcation B. The first and second therapeutic arms 906a and 906b may also include magnets and/or other suitable mechanisms to draw the energy delivery elements 908 toward the bifurcation B in alignment with one another or offset from one another.

As further shown in FIG. 9, the catheter assembly 900 can also optionally include an expandable member 942 (e.g., an inflatable balloon) at the second therapeutic arm 906b proximal to the second energy delivery element 908b. When energy is delivered in a bipolar electric field, the expandable member 942 can be used to at least partially occlude blood flow through the second branch BR2, and thereby inhibit or interrupt electrical current that may flow through the blood. This forces the current path through the adventitia of the branches BR where the concentration of renal nerves lies, and therefore enhances neuromodulation. To enhance cooling effects typically provided by the flowing blood, the catheter assembly 900 can be configured to deliver (e.g., inject) a cooling fluid (e.g., saline) proximate the second energy delivery element 908b before or during energy delivery. The expandable member 942 may also be used to anchor or stabilize the second therapeutic arm 906b during energy delivery and/or to press or bias the second energy delivery element 908 into contact with the vessel wall. In other embodiments, the expandable member 942 can be at the first therapeutic arm 906b proximal to the first energy delivery element 908a and/or the catheter assembly 900 can include more than one expandable member 942.

Figure 10:
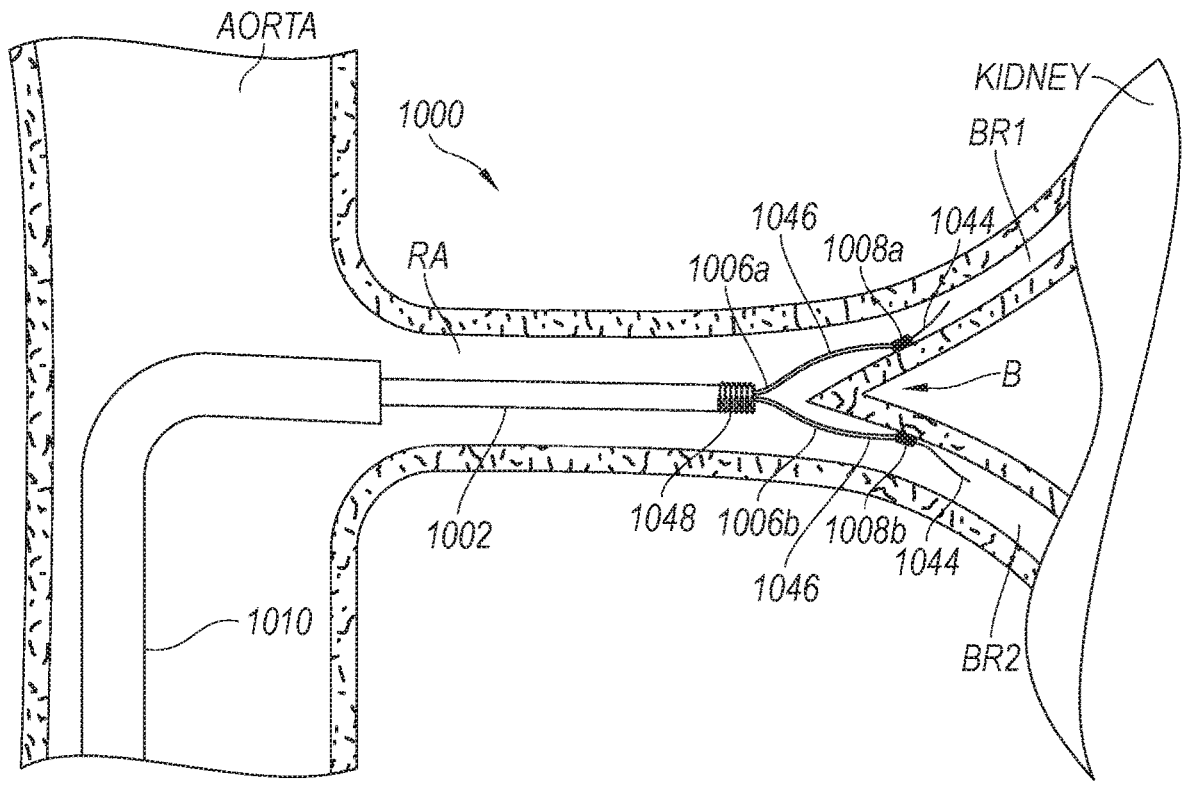
FIG. 10 is a partial cross-sectional view of a distal portion of a catheter assembly proximate a renal artery bifurcation in accordance with an additional embodiment of the present technology.

FIG. 10 is a partial cross-sectional view of a distal portion of a catheter assembly 1000 configured in accordance with yet another embodiment of the present technology. The catheter assembly 1000 includes features generally similar to the features of the catheter assemblies described above. In the embodiment illustrated in FIG. 10, however, first and second therapeutic arms 1006a and 1006b (referred to collectively as "therapeutic arms 1006") each include deflectable tip portion 1044 distal to an energy delivery element 1008 (identified as a first energy delivery element 1008a and a second energy delivery element 1008b) and a semi-rigid or flexible portion 1046 proximal to the energy delivery element 1008. The deflectable tip portions 1044 can be highly flexible and/or soft to deflect off of vessel walls and ease delivery of the therapeutic arms 1006 into the branches BR. The flexible portion 1046 can be stiffer than the deflectable tip portions 1044 to force or otherwise position the energy delivery elements 1008 in stable contact against the vessel walls extending distally the bifurcation B. For example, in certain embodiments, the flexible portions 1046 can be made from a pre-shaped wire configured to direct the energy delivery elements 1008 toward one another in accordance with the vascular structure proximate the bifurcation B. The first and second therapeutic arms 1006a and 1006b may be positioned simultaneously within the respective branches BR of the renal artery RA, or each therapeutic arm 1006 may be inserted separately. Once positioned against the vessel walls, the energy delivery elements 1008 can deliver therapeutically-effective energy to the nerves proximate the bifurcation 13. When the energy delivery elements 1008 are configured to deliver energy in the form of a bipolar energy field, the catheter assembly 1000 may also include a return electrode 1048 electrically coupled to the energy delivery elements 1008 at a distal portion of shaft 1002.

IV. Neuromodulation Catheter Assemblies for Intra-to-Extravascular Delivery

Figure 11:
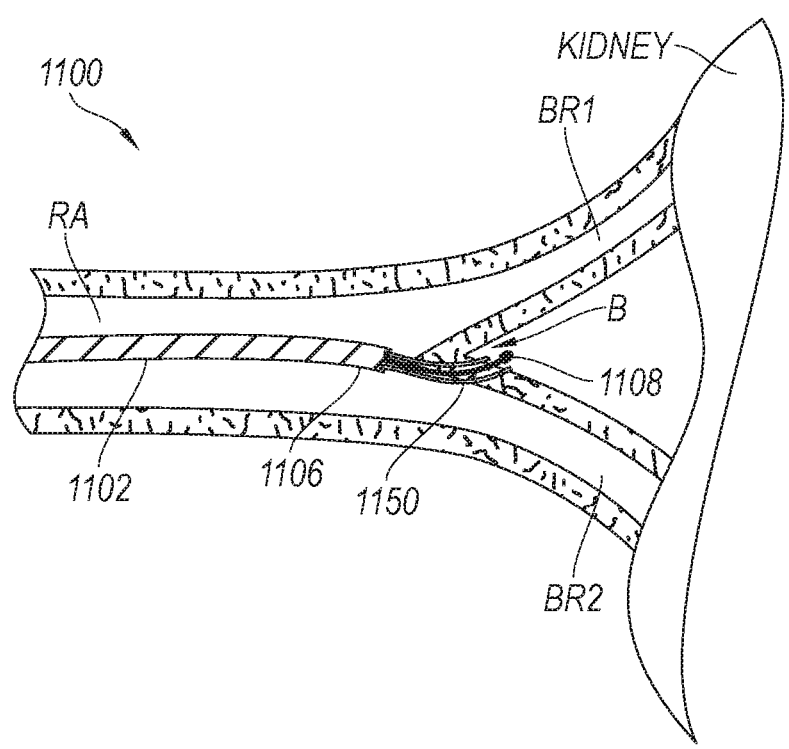
FIG. 11 is a partial cross-sectional view of a distal portion of an inter-to-extravascular catheter assembly proximate a renal artery bifurcation in accordance with an embodiment of the present technology.

FIG. 11 is a partial cross-sectional view of a distal portion of a catheter assembly 1100 proximate a renal artery bifurcation B and configured in accordance with another embodiment of the present technology. The catheter assembly 1100 includes several features generally similar to the catheters described above. However, as shown in FIG. 11, the catheter assembly 1100 includes a single therapeutic arm 1106 extending from a shaft 1102 and carrying an energy delivery element 1108. The therapeutic arm 1106 can be delivered to the treatment site using a guide wire or steerable features integrated with the therapeutic arm 1106. At the treatment site, the therapeutic arm 1106 can be configured to deliver the energy delivery element 1108 from a lumen of the renal artery RA (e.g., the one of the branches BR) into adventia of the renal artery RA or to an extravascular space proximate the carina of the bifurcation B. For example, the therapeutic arm 1106 can include a cannula 1150 through which a needle (not shown) can extend to puncture or otherwise form a small opening through at least a portion of the vessel wall proximate the bifurcation B. The energy delivery element 1108 (e.g., an electrode made of a flexible bundle of coils) can then be delivered through the cannula 1150 into the adventitia of the vessel wall or extravascular space proximate the bifurcation B to apply energy to the proximal nerves. In other embodiments, the catheter assembly 1100 can include other suitable structures for delivering the energy delivery element 1108 through the vessel walls into the extravascular space. Additional features related to intra-to-extravascular energy delivery are disclosed in commonly-assigned U.S. Pat. No. 7,620,451, filed on Feb. 27, 2006, and entitled "METHODS AND APPARATUS FOR PULSED ELECTRIC FIELD NEUROMODULATION VIA AN INTRA-TO-EXTRA VASCULAR APPROACH," which is herein incorporated by reference in its entirety.

In certain embodiments, the catheter assembly 1100 can include a second therapeutic arm (not shown) generally similar to the therapeutic arm 1106 shown in FIG. 11. The second therapeutic arm can be configured to provide extravascular neuromodulation via an opposite branch BR1 as the therapeutic arm 1106, and therefore provide extravascular neuromodulation at both sides of the bifurcation B. In other embodiments, the therapeutic arm 1106 can be combined with any of the intravascular therapeutic arms described above to deliver neuromodulation energy to both sides of the bifurcation B. The catheter assembly 100 can alternatively include a second shaft or arm that does not include an energy delivery element, but includes a feature, such as a magnet, that is configured to draw the energy delivery element 1108 and the cannula 1150 toward a vessel wall extending from the bifurcation B to facilitate access to the adventitia and/or extravascular space proximate the bifurcation B.

V. Neuromodulation Catheter Assemblies for Multi-Vessel Delivery

Figure 12:
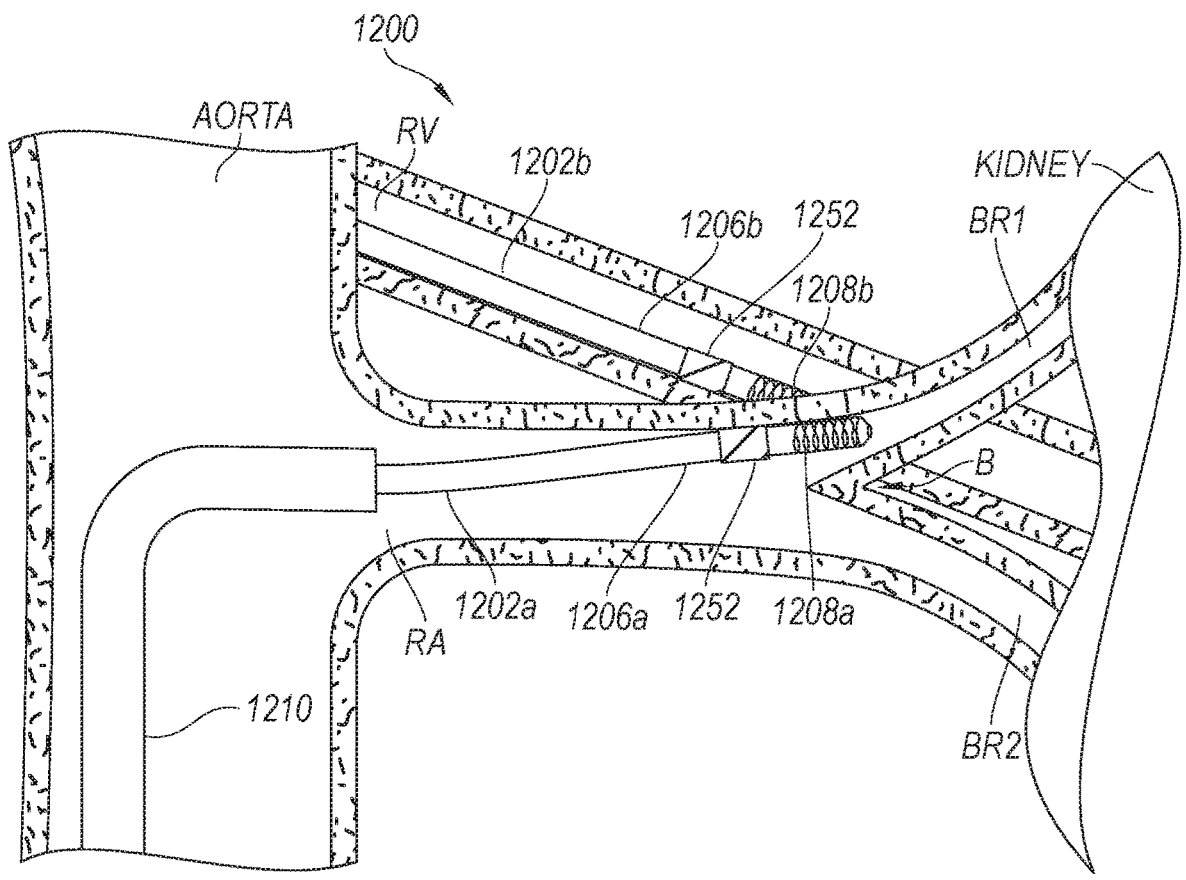
FIG. 12 is a partial cross-sectional view of a distal portion of a multi-vessel catheter assembly for neuromodulation within a renal artery and a renal vein proximate a renal artery bifurcation in accordance with an embodiment of the present technology.

FIG. 12 is a partial cross-sectional view of a distal portion of a catheter assembly 1200 configured in accordance with a further embodiment of the present technology. The catheter assembly 1200 includes features generally similar to the features of the catheter assemblies described above, such as first and second therapeutic arms 1206a and 1206b (referred to collectively as "therapeutic arms 1206) carrying first and second energy delivery elements 1208a and 1208b, respectively (referred to collectively as "energy delivery elements 1208"), for therapeutically-effective modulation of nerves proximate a bifurcation or branch point of a vessel (e.g., the bifurcation B of the renal artery RA). However, in the embodiment illustrated in FIG. 12, each therapeutic arm 1206 defines a distal portion of a separate catheter or shaft 1202a or 1202b (identified individually as a first shaft 1202a and a second shaft 1202b, and referred to collectively as "shafts 1202") configured to be delivered to different vessels proximate a bifurcation of at least one of the vessels. For example, as shown in FIG. 12, the distal portion of the first shaft 1202a can be delivered to the renal artery RA proximate the bifurcation B, and the distal portion of the second shaft 1202b can be delivered to a renal vein (RV) proximate the bifurcation B of the renal artery RA. The first and second energy delivery elements 1208a and 1208b can be substantially aligned along an arterial wall proximate the bifurcation B as shown in FIG. 12, or may be offset from one another at the vessel walls.

As further shown in FIG. 12, the therapeutic arms 1206 can include complimentary magnetic features 1252 (e.g., each magnetic feature 1252 having a different polarity) proximate to the energy delivery elements 1208. The magnetic features 1252 can draw the energy delivery element 1208 toward one another against adjacent wall portions of the renal artery RA and the renal vein (RV) such that the energy delivery elements 1208 can apply therapeutically effective energy on either site of the nerves between the renal artery RA and renal vein (RV proximate the bifurcation B. In certain embodiments, one of the magnetic features 1252 includes two poles such that the magnetic features 1252 (and therefore the therapeutic arms 1206) repel one another as they are advanced through the vasculature toward the treatment site (e.g., proximate the bifurcation B). Once both therapeutic arms 1206 are at the treatment site, the shaft 1202 with the bipolar magnetic feature 1252 can be rotated or otherwise manipulated such that the two magnetic features 1252 are attracted to one another to draw the energy delivery elements 1208 together for wall contact. In other embodiments, the catheter assembly 1200 can include other features that facilitate contact with the walls of the renal artery RA and renal vein RV. The catheter assembly 1200, like the catheter assemblies described above, can apply therapeutically-effective energy to the concentration of nerves proximate the renal artery bifurcation B, and renal neuromodulation at such a region dense with renal nerves is expected to provide enhanced overall neuromodulation effects.

It will be appreciated that specific embodiments of the technology have been described herein for purposes of illustration, but that various modifications may be made without deviating from the disclosure. For example, many of the catheter assemblies described above include two therapeutic arms. However, any of the embodiments of the catheter assemblies can include a single therapeutic arm or more than two therapeutic arms. If more than two therapeutic arms are included in a catheter assembly, each therapeutic arm can define a distal portion of its own shaft, the therapeutic arms can extend from the same shaft, or the shaft and/or therapeutic arms may include one or more apertures (e.g., similar to the port 940 shown in FIG. 9) from which one or more therapeutic arms can be extended. In such multiple therapeutic arm embodiments, more than one therapeutic arm can be positioned in each branch BR of the renal artery RA. For example, one or more therapeutic arms can face outwardly away from the bifurcation B and one or more other therapeutic arms can face toward the bifurcation B. In other embodiments, multiple arms can be positioned at different target sites along the length of each branch BR, thereby neuromodulating multiple zones within each branch BR. In further embodiments, catheter assemblies can include a therapeutic arm corresponding to each branch vessel extending from a branch point (e.g., three therapeutic arms configured to be delivered to three branch vessels).

VI. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal modulation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 13:
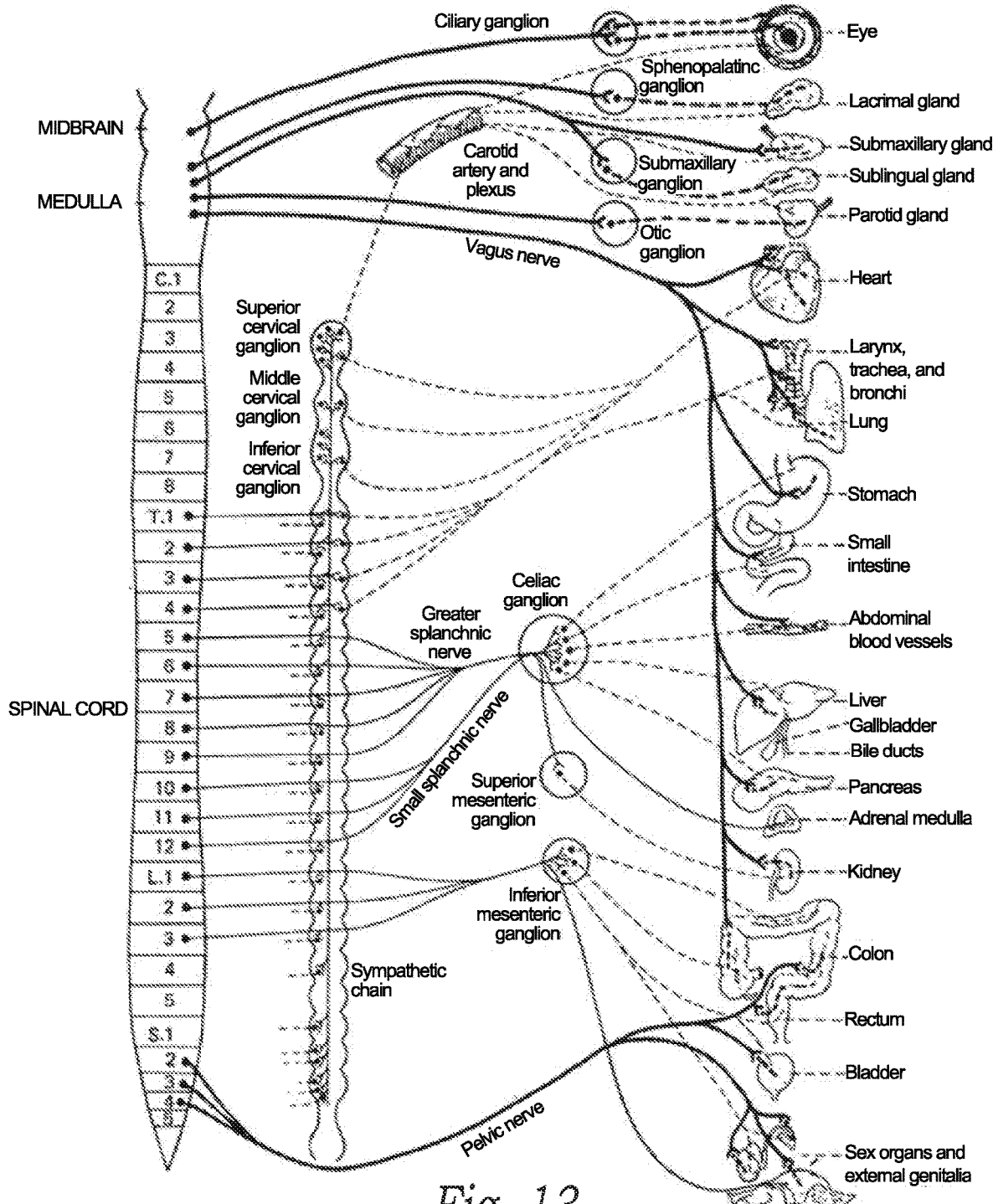
FIG. 13 is a conceptual illustration of the SNS and how the brain communicates with the body via the SNS.

As shown in FIG. 13, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 14:
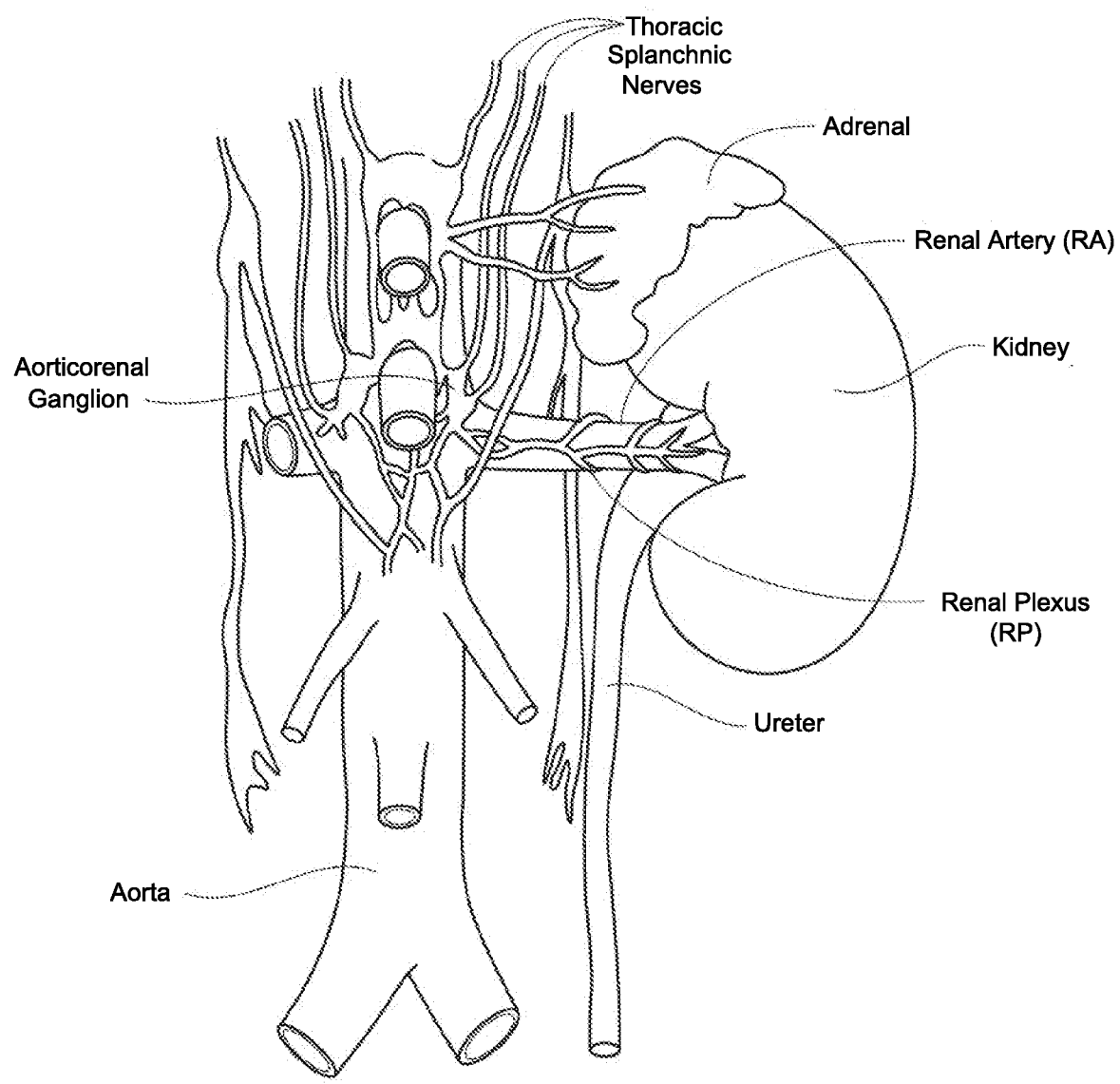
FIG. 14 is an enlarged anatomic view of nerves innervating a left kidney to form the renal plexus surrounding the left renal artery.

As shown in FIG. 14, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 15:
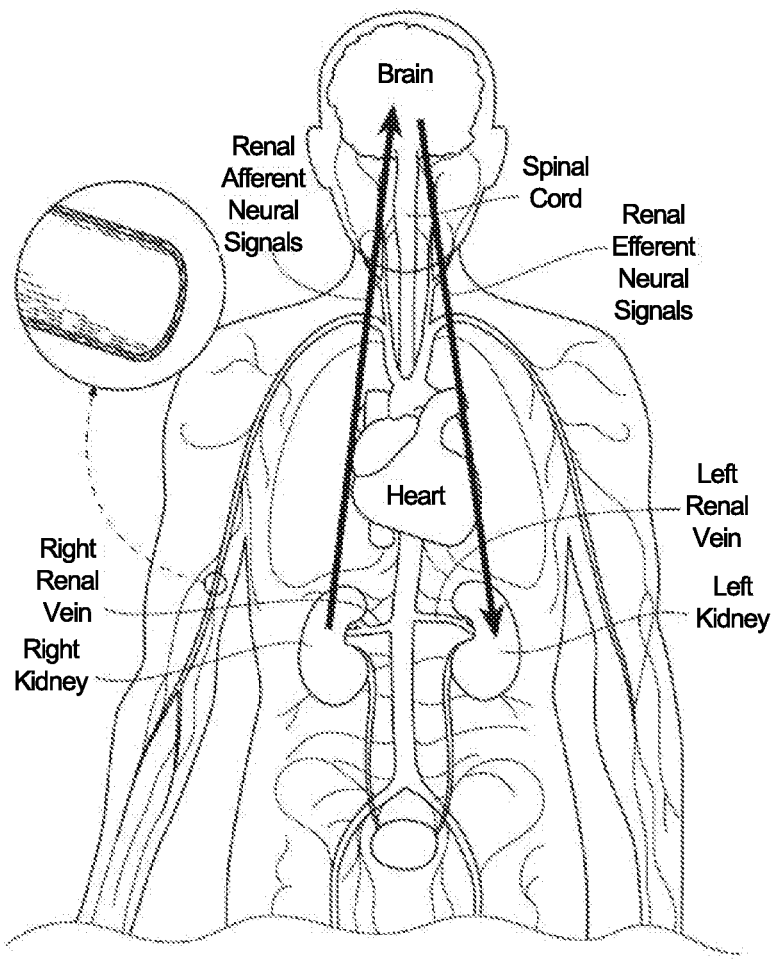
FIGS. 15 and 16 provide anatomic and conceptual views of a human body, respectively, depicting neural efferent and afferent communication between the brain and kidneys.
Figure 16:
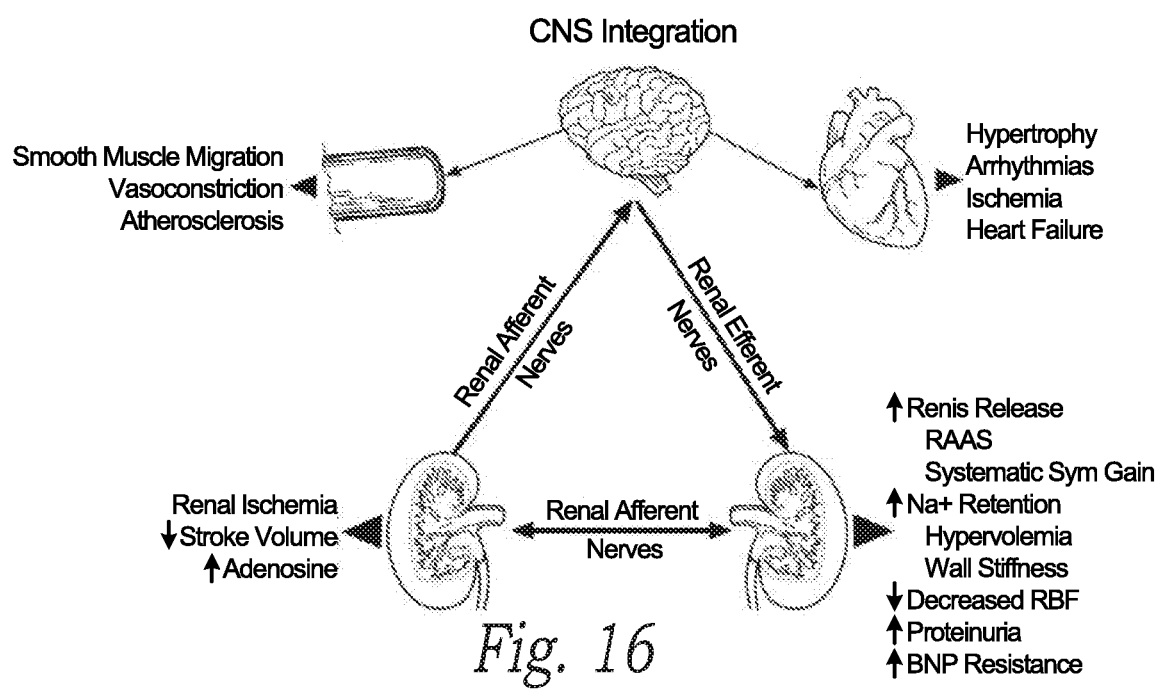

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 15 and 16, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 13. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figures 17, 18:
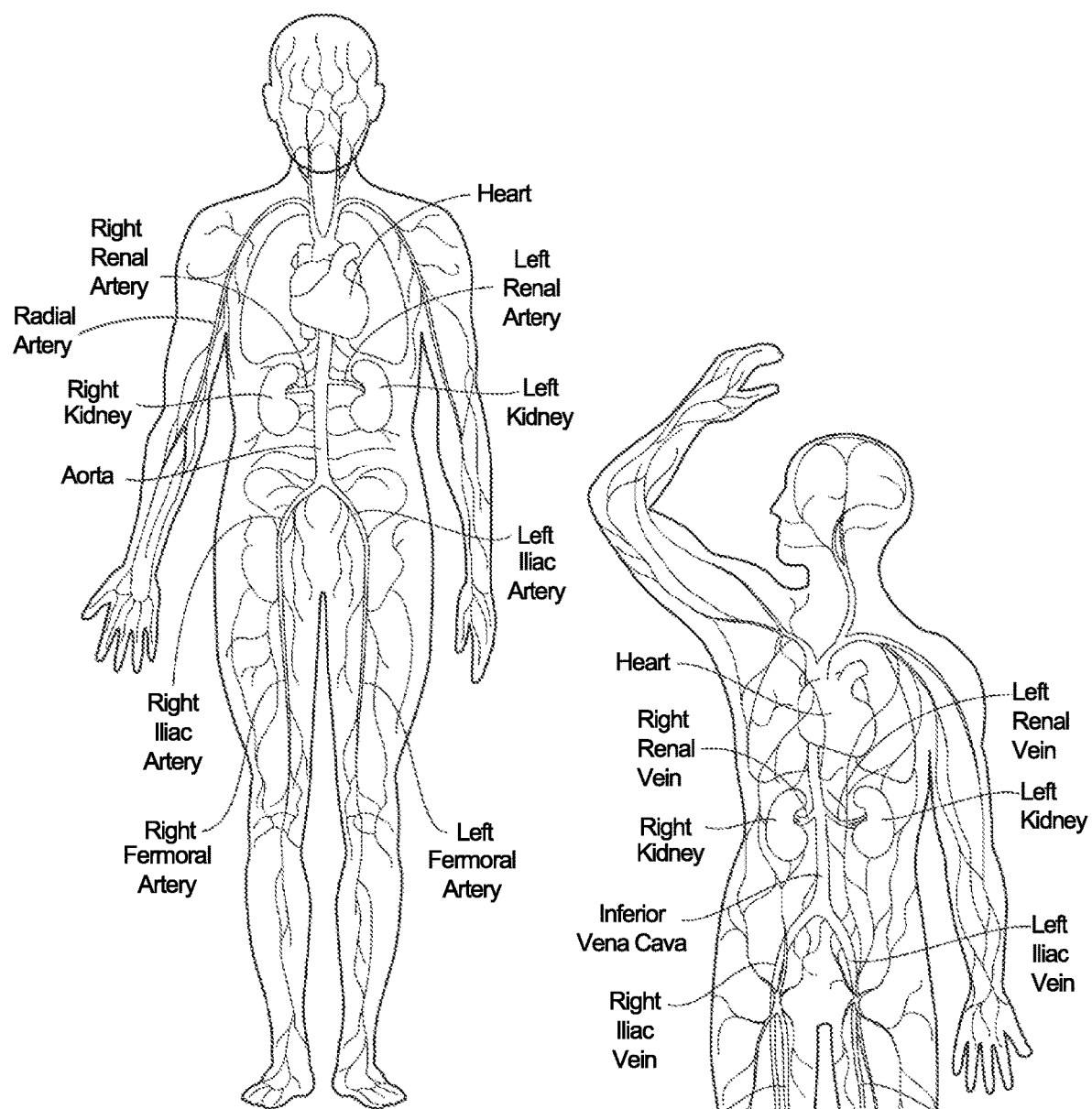
FIGS. 17 and 18 show the arterial vascular system and venous system of the human body, respectively.

In accordance with the present technology, neuromodulation of a left and/or right renal plexus RP, which is intimately associated with a left and/or right renal artery, may be achieved through intravascular access. As FIG. 17 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 18 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the takeoff angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; B distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal connectivity of blood flow past a vessel wall treatment site and/or radiative heat transfer; (e) renal artery motion relative to the aorta induced by respiration, patient movement, and/or blood flow pulsatility; and (f) the takeoff angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 10 cm (4 inches) cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the takeoff angle between the renal artery and the aorta may vary significantly between patients, and also may vary dynamically within a patient, e.g., due to kidney motion. The takeoff angle generally may be in a range of about 300-1350.

X. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, B all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of treating a human patient, the method comprising:
   advancing a distal portion of a catheter assembly proximate a bifurcation of a renal artery, wherein the distal portion of the catheter assembly includes a bifurcated shaft comprising a first therapeutic arm carrying a first energy delivery element and a second therapeutic arm carrying a second energy delivery element, wherein the first therapeutic arm comprises a first magnetic structure and the second therapeutic arm comprises a second magnetic structure, and wherein advancing the distal portion of the catheter assembly proximate the bifurcation of the renal artery comprises:
      delivering the first therapeutic arm into a first branch vessel proximate the bifurcation; and
      delivering the second therapeutic arm into a second branch vessel proximate the bifurcation;
   engaging a vessel wall at the bifurcation with the first energy delivery element and the second energy delivery element, wherein the engaging comprises drawing the first and second therapeutic arms toward one another such that the first energy delivery element engages a vessel wall of the first branch vessel and the second energy delivery element carried by the second therapeutic arm engages a vessel wall of the second branch vessel, wherein drawing the first and second therapeutic arms toward each one another comprises positioning the first magnetic structure in proximity with the second magnetic structure to draw the first and second energy delivery elements toward one another and engage the respective vessel walls of the first branch vessel and the second branch vessel; and applying therapeutically-effective energy to renal nerves proximate the bifurcation via the first energy delivery element and the second energy delivery element, wherein the applying therapeutically-effective energy to renal nerves proximate the bifurcation comprises applying therapeutically-effective energy to renal nerves from at least two treatment sites proximate the bifurcation.

2. The method of claim 1 wherein advancing the distal portion of the catheter assembly comprises advancing a distal portion of the bifurcated shaft proximate to the bifurcation of the renal artery.

3. The method of claim 1 wherein the first and second therapeutic arms are separated by an angle, and wherein the angle is less than a takeoff angle of the bifurcation of the renal artery.

4. The method of claim 1 wherein the first and second therapeutic arms separated by an angle, and wherein the angle corresponds to a takeoff angle of the bifurcation of the renal artery.

5. A neuromodulation catheter assembly, comprising:
a shaft configured for intravascular delivery to a treatment site proximate a branch point in a renal blood vessel of a human patient;
a first arm extending from a distal portion of the shaft, wherein the first arm includes a first electrode and a first magnetic element carried by the first arm; and
a second arm extending from the distal portion of the shaft, wherein the second arm includes a second electrode and a second magnetic element carried by the second arm,
wherein the first and second electrodes are configured to be positioned adjacent to vessel walls on opposing sides of the branch point of the renal blood vessel and the first magnetic element is configured to interact with the second magnetic element to draw the first and second electrodes toward one another and into apposition with vessel walls extending distally from the branch point,
wherein the first and second electrodes are configured to deliver radiofrequency (RF) energy to renal nerves proximate the branch point.

6. The neuromodulation catheter assembly of claim 5 wherein the first magnetic element extends along an inner diameter of the first arm and the second magnetic element extends along an inner diameter of the second arm.

7. The neuromodulation catheter assembly of claim 5 wherein the first magnetic element is embedded in the first arm and the second magnetic element is embedded in the second arm.

8. The neuromodulation catheter assembly of claim 5 wherein the first magnetic element is within the first electrode and the second magnetic element is within the second electrode.

9. The neuromodulation catheter assembly of claim 5 wherein the distal portion of the shaft bifurcates to define the first and second arms.

10. The neuromodulation catheter assembly of claim 9 wherein the distal portion of the shaft forms an angle at the bifurcation, and wherein the angle is less than an angle of the branch point.

11. The neuromodulation catheter assembly of claim 5 wherein:
the renal blood vessel is a renal artery with first and second branches extending from the branch point in the renal artery;
the first electrode is sized and shaped to be delivered into the first branch and contact a wall of the first branch; and
the second electrode is sized and shaped to be delivered into a second branch and contact a wall of the second branch.

12. A method of treating a human patient, the method comprising:
advancing a distal portion of a catheter assembly proximate a bifurcation of a renal artery, wherein the distal portion of the catheter assembly includes a bifurcated shaft comprising a first therapeutic arm carrying a first energy delivery element and a second therapeutic arm carrying a second energy delivery element, wherein the first therapeutic arm comprises a first magnetic structure and the second therapeutic arm comprises a second magnetic structure, and wherein advancing the distal portion of the catheter assembly proximate the bifurcation of the renal artery comprises:
delivering the first therapeutic arm to a first target location in a first branch vessel proximate the bifurcation; and
delivering the second therapeutic arm to a second target location in a second branch vessel proximate the bifurcation;
moving the first therapeutic arm while at the first target location in the first branch vessel such that the first energy delivery element moves from being spaced with a vessel wall of the first branch vessel into engagement with the vessel wall of the first branch vessel;
moving the second therapeutic arm while at the second target location in the second branch vessel such that the second energy delivery element moves from being spaced with a vessel wall of the second branch vessel into engagement with the vessel wall of the second branch vessel, wherein moving the first therapeutic arm and the moving the second therapeutic arm comprise drawing the first and second therapeutic arms toward one another by at least positioning the first magnetic structure in proximity with the second magnetic structure to draw the first and second energy delivery elements toward one another and engage the respective vessel walls of the first and second branch vessels; and
applying therapeutically-effective energy to renal nerves proximate the bifurcation via the first energy delivery element after the moving the first therapeutic arm and via the second energy delivery element after the moving the second therapeutic arm,
wherein applying therapeutically-effective energy to renal nerves proximate the bifurcation comprises applying therapeutically-effective energy to renal nerves from at least two treatment sites proximate the bifurcation.

13. The method of claim 12 wherein advancing the distal portion of the catheter assembly comprises advancing a distal portion of the bifurcated shaft proximate to the bifurcation of the renal artery.

14. The method of claim 12 wherein the first and second therapeutic arms are separated by an angle, and wherein the angle is less than a takeoff angle of the bifurcation of the renal artery.

15. The method of claim 12 wherein the first and second therapeutic arms separated by an angle, and wherein the angle corresponds to a takeoff angle of the bifurcation of the renal artery.

* * * * *